(12) United States Patent
Greelis

(10) Patent No.: US 10,575,941 B2
(45) Date of Patent: Mar. 3, 2020

(54) BICEPS REPAIR ANCHORS, TOOLS, AND SYSTEMS AND METHODS FOR USING THEM

(71) Applicant: John P. Greelis, Carlsbad, CA (US)

(72) Inventor: John P. Greelis, Carlsbad, CA (US)

(*) Notice: Subject to any disclaimer, the term of this patent is extended or adjusted under 35 U.S.C. 154(b) by 42 days.

(21) Appl. No.: 15/614,336

(22) Filed: Jun. 5, 2017

(65) Prior Publication Data

US 2018/0071080 A1 Mar. 15, 2018

Related U.S. Application Data

(60) Provisional application No. 62/393,437, filed on Sep. 12, 2016.

(51) Int. Cl.
*A61F 2/08* (2006.01)
*A61B 17/04* (2006.01)
*A61B 17/00* (2006.01)

(52) U.S. Cl.
CPC ........ *A61F 2/0811* (2013.01); *A61B 17/0401* (2013.01); *A61F 2/0805* (2013.01); *A61B 2017/00358* (2013.01); *A61B 2017/0403* (2013.01); *A61B 2017/0404* (2013.01); *A61B 2017/0409* (2013.01); *A61B 2017/0453* (2013.01); *A61B 2017/0459* (2013.01); *A61B 2017/0464* (2013.01); *A61F 2002/0829* (2013.01); *A61F 2002/0835* (2013.01); *A61F 2002/0852* (2013.01); *A61F 2002/0858* (2013.01); *A61F 2002/0888* (2013.01); *A61F 2002/0894* (2013.01)

(58) Field of Classification Search
CPC .. A61F 2/0811; A61F 2002/0823; A61F 2/08; A61B 17/0401
See application file for complete search history.

(56) References Cited

U.S. PATENT DOCUMENTS

| | | | | |
|---|---|---|---|---|
| 5,084,050 A | * | 1/1992 | Draenert | A61F 2/30767 606/304 |
| 5,268,001 A | * | 12/1993 | Nicholson | A61B 17/0401 606/104 |
| 5,464,427 A | * | 11/1995 | Curtis | A61B 17/0401 411/60.1 |
| 5,649,963 A | * | 7/1997 | McDevitt | A61B 17/0401 606/232 |

(Continued)

*Primary Examiner* — Bruce E Snow
(74) *Attorney, Agent, or Firm* — William A. English; Vista IP Law Group LLP

(57) ABSTRACT

Tissue anchors and systems and methods for delivering and removing them are provided. In an exemplary embodiment, the tissue anchor may include an outer shell including a proximal end, a distal end, a passage extending therebetween, and a plurality of expandable arms; an expander including a proximal portion disposed within the passage and distal portion that extends distally from the outer shell distal, the expander movable proximally relative to the outer shell to a deployed position wherein the distal portion directs the plurality of arms outwardly to engage adjacent bone. A fork extends from the distal portion of the expander including a pair of tines spaced apart from one another and a concave distal surface extending between the tines. A suture loop extends from the distal portion of the expander for capturing a tissue structure.

12 Claims, 26 Drawing Sheets

(56) References Cited

U.S. PATENT DOCUMENTS

| | | | | |
|---|---|---|---|---|
| 5,725,529 | A * | 3/1998 | Nicholson | A61B 17/0401 606/232 |
| 5,728,136 | A * | 3/1998 | Thal | A61B 17/0401 606/232 |
| 6,527,794 | B1 * | 3/2003 | McDevitt | A61B 17/0401 606/1 |
| 6,641,596 | B1 * | 11/2003 | Lizardi | A61B 17/0401 606/232 |
| 9,615,820 | B2 * | 4/2017 | Mayer | A61B 17/0401 |
| 2002/0040241 | A1 * | 4/2002 | Jarvinen | A61F 2/0811 623/13.14 |
| 2011/0112550 | A1 * | 5/2011 | Heaven | A61B 17/0401 606/139 |
| 2013/0035721 | A1 * | 2/2013 | Brunelle | A61B 17/0401 606/232 |
| 2014/0249579 | A1 * | 9/2014 | Heaven | A61B 17/0401 606/232 |
| 2015/0190130 | A1 * | 7/2015 | Groh | A61B 17/0401 606/232 |

* cited by examiner

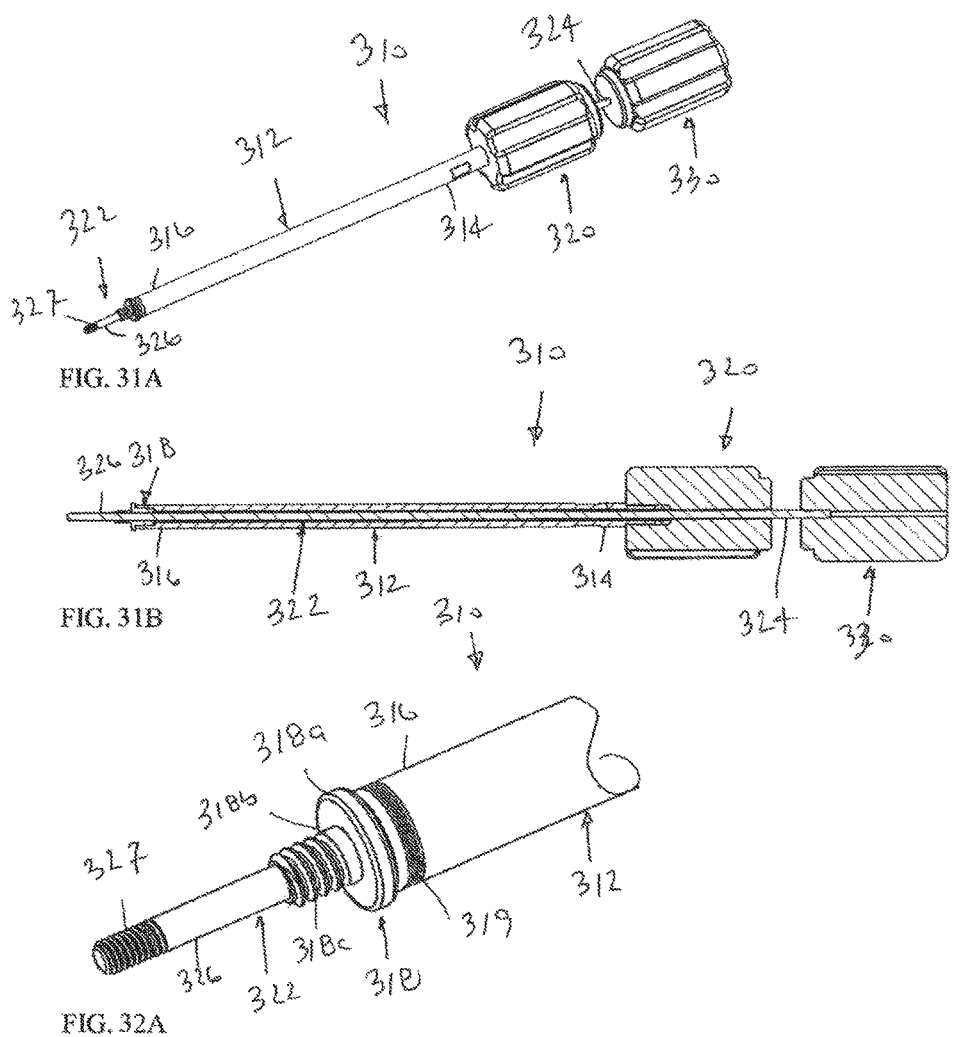

BICEPS REPAIR ANCHORS, TOOLS, AND SYSTEMS AND METHODS FOR USING THEM

RELATED APPLICATION DATA

This application claims benefit of U.S. provisional application Ser. No. 62/393,437, filed Sep. 12, 2016, the entire disclosure of which is expressly incorporated by reference herein.

FIELD OF THE INVENTION

The field of the invention generally relates to implantable anchors, delivery devices, and retrieval devices, and to systems and methods for using such anchors and devices.

BACKGROUND

There are many medical procedures that involve attaching tissue, such as a tendon, to bone. One common example is a torn rotator cuff, where the supraspinatus tendon has separated from the humerus. To repair a torn rotator cuff, a surgical procedure may be used to suture the torn tendon to the bone. Some procedures utilize large incisions and involve complete detachment of the deltoid muscle from the acromion. Small diameter holes are made in the bone for passing suture material through the bone to secure the tendon. Such large incision procedures are traumatic, causing prolonged pain and recovery time. Alternatively, arthroscopic techniques may be used to attach sutures using either small diameter holes or a bone anchor. However, it can be difficult to manipulate sutures within the surgical site using arthroscopic techniques. In addition, when knot tying is used to secure the suture to a bone anchor, it may be difficult to properly adjust the tension of the suture while tightening the knot.

Therefore, devices, systems, and methods that facilitate attaching soft tissue to bone, e.g., during an arthroscopic procedure, would be useful.

SUMMARY

The present application generally relates to implantable anchors, delivery devices, and retrieval devices, and to systems and methods for using such anchors and devices. For example, the present invention may include.

In accordance with an exemplary embodiment, a tissue anchor is provided for securing a tissue structure to bone that includes an outer shell including a proximal end, a distal end sized for introduction into a bore in bone, a passage extending between the proximal and distal ends defining a longitudinal axis therebetween, a pair of opposing planar surfaces extending at least partially between the proximal and distal ends, and a plurality of distal slots extending proximally from the distal end to define a plurality of expandable arms; an expander including a uniform cross-section proximal portion and a ramped distal portion, the proximal portion disposed within the passage such that the distal portion extends distally from the outer shell distal end in a delivery position, the expander movable proximally relative to the outer shell to a deployed position wherein the distal portion enters the passage, thereby directing the plurality of arms outwardly to engage bone adjacent the bore; and a suture loop extending from the distal portion of the expander for capturing a tissue structure.

In accordance with another embodiment, a tissue anchor is provided for securing a tissue structure to bone that includes an outer shell including a proximal end, a distal end sized for introduction into a bore in bone, a passage extending between the proximal and distal ends defining a longitudinal axis therebetween, and a plurality of expandable arms; an expander including a uniform cross-section proximal portion and a ramped distal portion, the proximal portion disposed within the passage such that the distal portion extends distally from the outer shell distal end in a delivery position, the expander movable proximally relative to the outer shell to a deployed position wherein the distal portion enters the passage, thereby directing the plurality of arms outwardly to engage bone adjacent the bore; a fork extending distally from the distal portion of the expander, the fork including a pair of tines spaced apart from one another and a concave distal surface extending between the tines; and a suture loop extending from the distal portion of the expander for capturing a tissue structure.

In accordance with still another embodiment, a tissue anchor is provided for securing a tissue structure to bone that includes an outer shell including a proximal end, a distal end sized for introduction into a bore in bone, a passage extending between the proximal and distal ends defining a longitudinal axis therebetween, a plurality of expandable arms, each of the arms including a first end coupled to the outer shell to provide a hinge and a second free end disposed proximal to the first end, the free end configured to be directed radially outwardly away from the central axis as the expander moves to the deployed position; an expander including a proximal portion and a distal portion, the proximal portion disposed within the passage such that the distal portion extends distally from the outer shell distal end in a delivery position, the expander movable proximally relative to the outer shell to a deployed position wherein the distal portion enters the passage, thereby directing the plurality of arms outwardly to engage bone adjacent the bore; and a suture loop extending from the distal portion of the expander for capturing a tissue structure. Optionally, the outer shell may include planar side surfaces and/or other asymmetric cross-section and/or the expander may include a fork.

In accordance with yet another embodiment, a system is provided for securing a tissue structure to bone that includes a tissue anchor including an outer shell and an expander movable from a delivery position to a deployed position to expand arms on the outer shell to engage adjacent bone, and a delivery tool. The delivery tool may include an outer shaft including a proximal end coupled to a handle and a distal end disposed adjacent the proximal end of the outer shell; an inner shaft coaxially disposed within the outer shaft and including a proximal end and a distal end extending from the outer shaft distal end and coupled to the proximal portion of the expander; and an actuator coupled to the inner shaft proximal end for directing the inner shaft from a distal position to a proximal position, thereby directing the expander from the delivery position to the deployed position.

In accordance with another embodiment, a method is provided for securing a tissue structure to bone that includes providing a tissue anchor including an outer shell, an expander including a proximal portion disposed within a passage in the outer shell and a distal portion extending from the outer shell, and a suture loop extending from the distal portion; receiving a tissue structure in the suture loop; introducing the distal portion of the expander and the outer shell into a bore in bone to position the tissue structure within the bore; directing the expander proximally relative to the outer shell from a delivery position to a deployed position wherein the distal portion causes arms on the outer shell to expand outwardly to engage bone adjacent the bore; and removing excess suture material extending from the bore. Optionally, the expander may include a fork extending from its distal end, and the tissue structure may be further engaged within the bore by the fork. In addition or alternatively, the outer shell may include opposing planar surfaces and the tissue structure may extend along the planar surfaces out of the bore.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

FIG. 6 is a cross-sectional view of the tissue anchor and shaft taken along plane 5-5 shown in FIG. 3.

FIGS. 31A and 31B are perspective and cross-sectional views, respectively, of another embodiment of a removal tool.

FIGS. 32A and 32B are details of alternative embodiments of tips that may be provided on the removal tool of FIGS. 31A and 31B.

DETAILED DESCRIPTION OF THE EXEMPLARY EMBODIMENTS

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Turning to the drawings, FIGS. 1-6 show an exemplary embodiment of a system 8 including a tissue anchor 50

Figure 1:
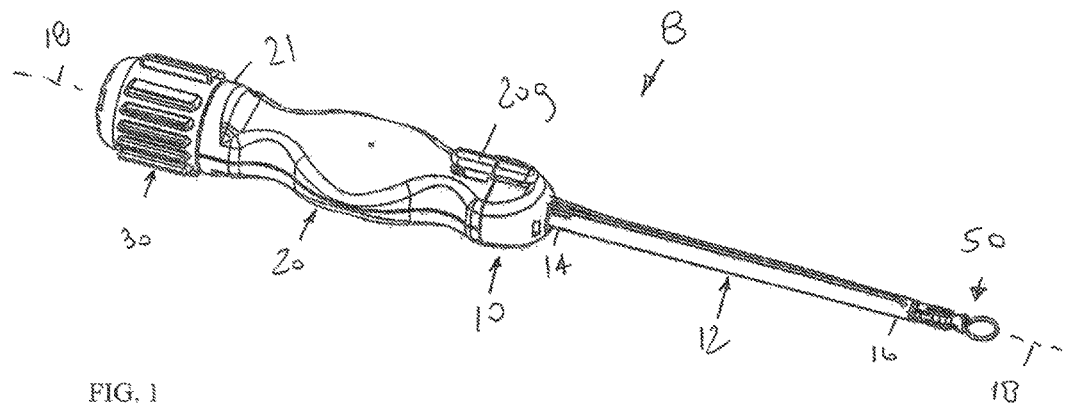
FIG. 1 is a perspective view of an exemplary embodiment of a system for attaching tissue to bone including a tool including a shaft carrying a tissue anchor.

(which, optionally, may be any of the embodiments described herein) and a delivery tool 10 for introducing and deploying the anchor 50. Generally, the delivery tool 10 includes an elongate outer shaft 12 including a proximal end 14 coupled to a handle 20 and a distal end 16, as best seen in FIGS. 1 and 2A, and an elongate inner shaft 22 including a proximal end 24 coupled to an actuator 30 and a distal end 26 extending from the outer shaft distal end 16, e.g., as best seen in FIG. 6. The distal ends 16, 26 may be detachably coupled to the anchor 50, to allow delivery and deployment of the anchor 50, as described further below.

With particular reference to FIGS. 3-6, the tissue anchor 50 generally includes an expandable outer shell 52, an expander 70, and a length of suture 90. The outer shell 52 and expander 70 may be formed from similar and/or compatible material, e.g., plastic, metal, or composite material. In an exemplary embodiment, the outer shell 52 may be formed from plastic, such as PEEK, that allows the outer shell 52 to be plastically expanded and/or otherwise deformed during deployment of the anchor 50. The expander 70 may be formed from substantially rigid material, e.g., plastic, metal, or composite materials, that may retain its shape during deployment of the anchor 50. The suture 90 may be formed from an elongate filament, e.g., formed from plastic, metal, composite, or other materials, such as braided suture, monofilament suture, wire, or other small chord or flexible rod.

The outer shell 52 is a tubular body including a proximal end 54, a distal end 56, and a passage 58 extending between the proximal and distal ends 54, 56. A plurality of axial slots 60 extend through the outer shell 52 proximally from the distal end 56 partially towards the proximal end 54, thereby defining a plurality of expandable arms 62 adjacent the distal end 56. For example, in the embodiment shown in FIGS. 3 and 4A, the outer shell 52 may include four distal slots 60 and four arms 62.

Optionally, as shown, the distal end 56 may include a beveled or other tapered surface 56a, e.g., to provide tapered tips for the arms 62. In addition or alternatively, the outer shell 52 may include a plurality of axial slots 64 extending distally from the proximal end 54 partially towards the distal end 56, e.g., offset circumferentially relative to the distal slots 60. The proximal slots 64 may expand partially during expansion of the arms 62, e.g., to enhance securing the proximal end 54 to cortical bone, as described further elsewhere herein.

Figure 5A:
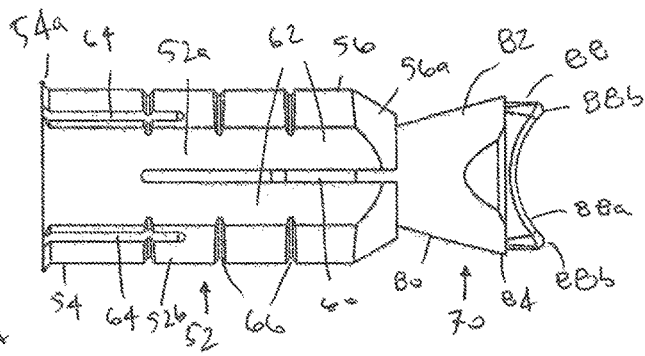
FIG. 5A is a side view of the tissue anchor of FIG. 3.
Figure 5B:
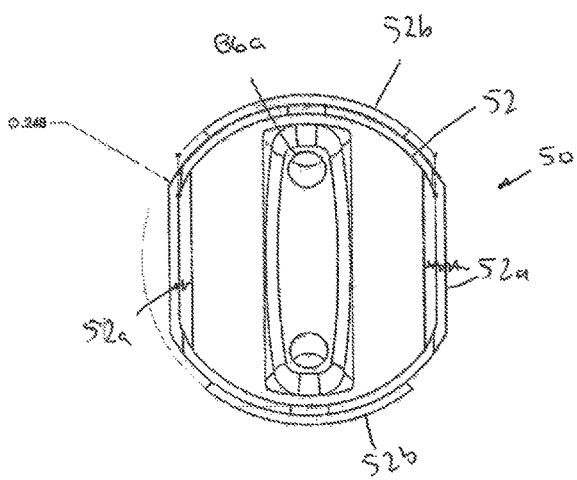
FIG. 5B is an end view of the tissue anchor of FIG. 3.

In addition, as shown in FIGS. 5A and 5B, the outer shell 52 has a partially cylindrical cross-section extending from the proximal end 54 towards the distal end 56, e.g., to the tapered surface 56a, i.e., defining a pair of substantially planar side surfaces 52a on opposite sides of the outer shell 52. Thus, the outer shell 52 includes rounded side surfaces 52b between the planar side surfaces 52a, e.g., defining an outer diameter for the outer shell 52, while the planar side surfaces 52a define recesses within the outer diameter, as can be seen in FIG. 6.

Figure 3:
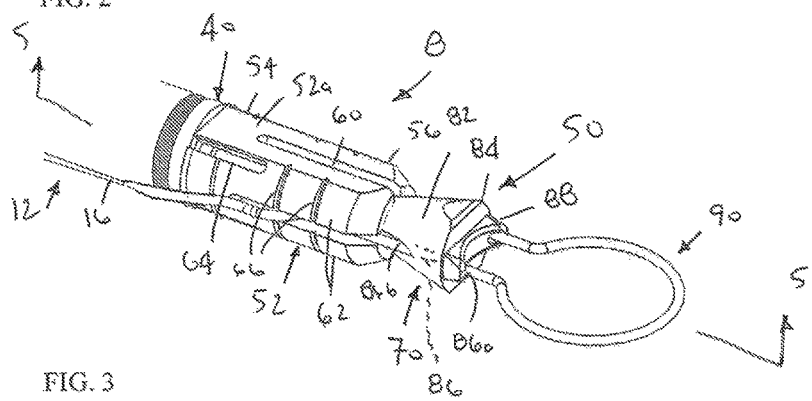
FIG. 3 is a perspective view of an exemplary embodiment of a tissue anchor carried on the distal end of the shaft of FIG. 1.
Figure 4:
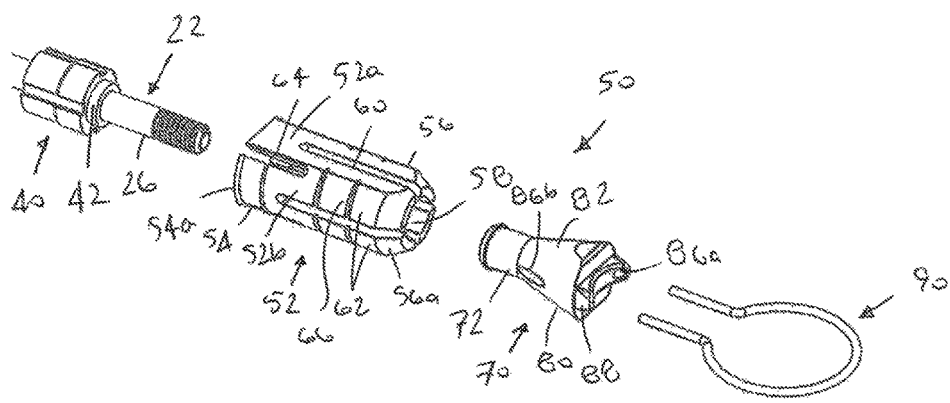
FIG. 4 is an exploded view of the tissue anchor of FIG. 3. showing an expandable outer shell, expander, and suture loop of the tissue anchor.
Figure 20A:
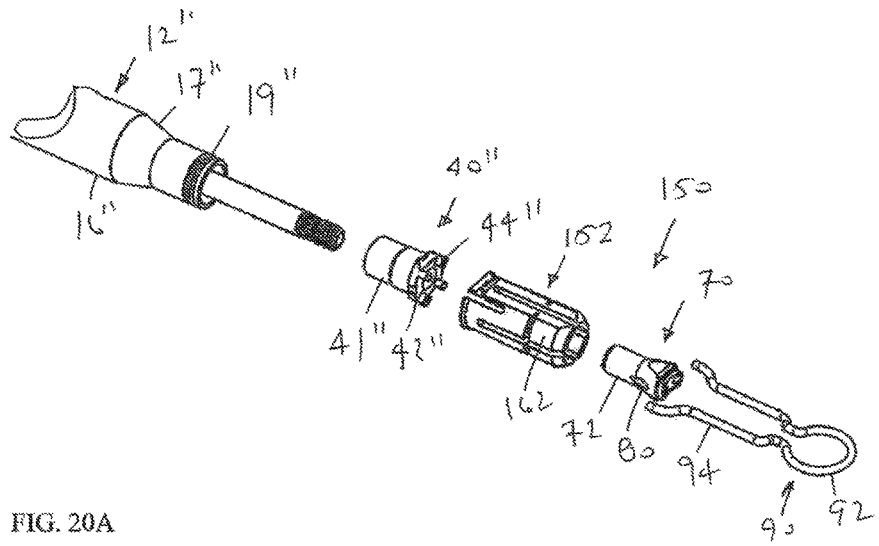
FIGS. 20A-20C are details showing yet another example of an interface for coupling a smaller tissue anchor to a delivery tool.
Figure 20B:
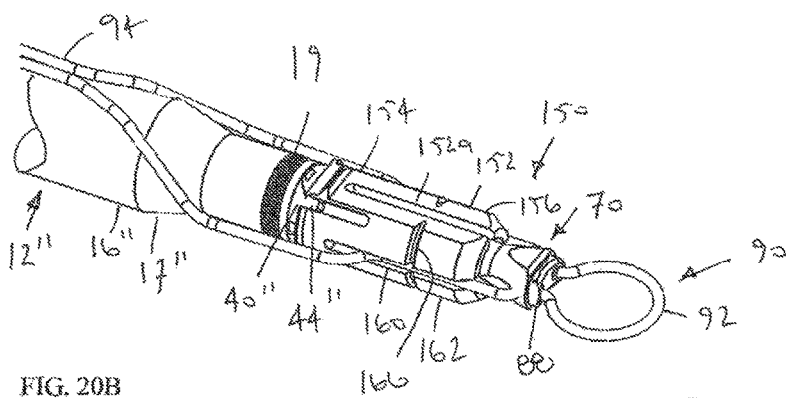
Figure 20C:
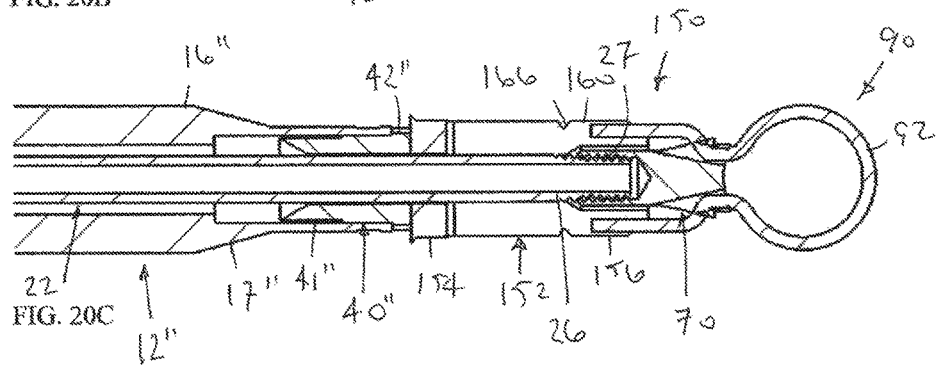

Optionally, the arms 62 may include one or more features to facilitate expansion of the arms 62 and/or engagement with adjacent bone or other tissue. For example, as best seen in FIGS. 3 and 4, the rounded side surfaces 52b may include one or more circumferential grooves or hinges 66, which may facilitate expansion of the arms 62, e.g., allowing the arms 62 to hinge or fold outwardly at the hinges 66, as described further elsewhere herein. In the embodiment shown in FIGS. 3 and 4, the arms 62 may include two hinges 66 spaced apart axially from one another along the length of the arms 62. Alternatively, as shown in FIGS. 20A-20C, a tissue anchor 150 is shown including an outer shell 152 where each arm 162 includes only a single hinge 166. For example, for smaller anchors, e.g., about 4.5 mm outer diameter, only a single hinge 166 may be provided on each arm 162, while for larger anchors, e.g., about 6.0 mm outer diameter, two hinges 66 may be provided on each arm 62. It will be appreciated that more than two hinges (not shown) may be provided, as desired.

Figure 11:
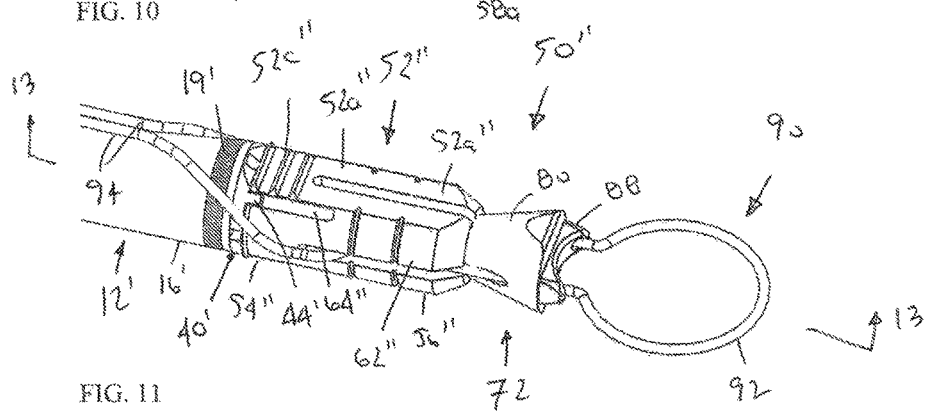
FIG. 11 is a perspective view of yet another embodiment of a tissue anchor carried on a distal end of a tool shaft.

In addition or alternatively, the outer shell 52 may include one or more outwardly projecting ribs, barbs, and the like (not shown), which may enhance engagement with adjacent bone. For example, FIG. 11 shows another embodiment of an anchor 50" including an outer shell 52" having a plurality of ribs 52c" that extend outwardly from the planar surface 52a" to engage adjacent bone. In alternative embodiments, the rounded surfaces 52b and/or the arms 62 may include one or more ribs, barbs, or other features (not shown) extending outwardly to engage adjacent bone.

Optionally, as best seen in FIGS. 3 and 4, the proximal end 54 of the outer shell 52 may include an annular ridge or flange 54a that extends outwardly, e.g., around the rounded side surfaces 52b, to seat the proximal end 54 against an outer surface of a bone into which the anchor 50 is inserted.

Returning to FIGS. 3-6, with particular reference to FIG. 4, the expander 70 includes a uniform cross-section proximal portion 72 and a tapered or ramped distal portion 80. The proximal portion 72 is sized to be slidably received within the passage 58 of the outer shell 52, e.g., into the distal end 56. For example, the proximal portion 72 and the passage 58 may have similar cross-sectional shapes, e.g., a circular shape, or an asymmetrical shape, e.g., an oval, square, rectangular, or other shape. Such an asymmetrical shape may allow the proximal portion 72 to slide axially within the passage 58 while preventing the expander 70 from rotating relative to the outer shell 52.

Optionally, the proximal portion 72 may also include one or more features for cooperating with the distal end 26 of the inner shaft 22, e.g., to couple movement of the expander 70 to the inner shaft 22. For example, as best seen in FIG. 6, the proximal portion 72 may include a proximal end 74 defining a recess 76 having helical inner threads 77 and the distal end 26 of the inner shaft 22 may include cooperating outer threads 27 such that the distal end 26 may be threaded into the recess 76. In an exemplary embodiment, 2-64 threads may be provided within the recess 76, although alternatively, 0-80, 1-72, or custom threads may be provided, as desired, e.g., to unwind the expander 70 from the inner shaft 22 faster, as described elsewhere herein.

Once the threads 77, 27 are engaged, axial movement of the expander 70 may be coupled to movement of the inner shaft 22. It will be appreciated that other connectors may be provided, as desired, e.g., cooperating detents, expandable collets, and the like (not shown), to couple the expander 70 to the inner shaft 26 and/or release the expander 70, as desired.

The distal portion 80 flares outwardly from the proximal portion 72, e.g., having a frusto-conical shape, to define a ramped outer surface 82 that terminates at a distal end 84 of the expander 70, e.g., defining an outer diameter or other cross-section larger than the passage 58 in the outer shell 52. For example, as shown in FIG. 5B, the distal portion 80 have an oval shape, e.g., flat oval or elliptical cross-section, defining a major axis and a minor axis perpendicular to and smaller than the major axis. In addition, the ramped distal portion 80 includes a pair of passages 86 extending from distal openings 86*a* distally to side openings 86*b* in the outer surface 82, e.g., for receiving the suture 90, as described further below.

In addition, the distal end 84 may include a fin or fork 88 defining a curved distal surface 88*a* between tips 88*b*. The fork 88 may have a width aligned with and similar to the major axis of the distal end 84 such that the fin 88 extends transversely across the distal end 84, e.g., within a plane parallel to the planar surfaces 52*a* of the outer shell 52, and a thickness smaller than the distal end 84, as described further below. The distal openings 86*a* of the passages 86 may be located in the curved distal surface 88*a* adjacent the tips 88*b*, e.g., as best seen in FIG. 6. Alternatively, the distal openings may be provided in the distal end 84 of the ramped distal portion, e.g., adjacent the tips if the fork has a smaller width than the distal end 84 (not shown). In a further alternative, the suture 90 may be omitted from the anchor 50 and the fork 88 may be sufficient to engage and/or introduce a tissue structure into a bore, as described further elsewhere herein.

Figure 16:
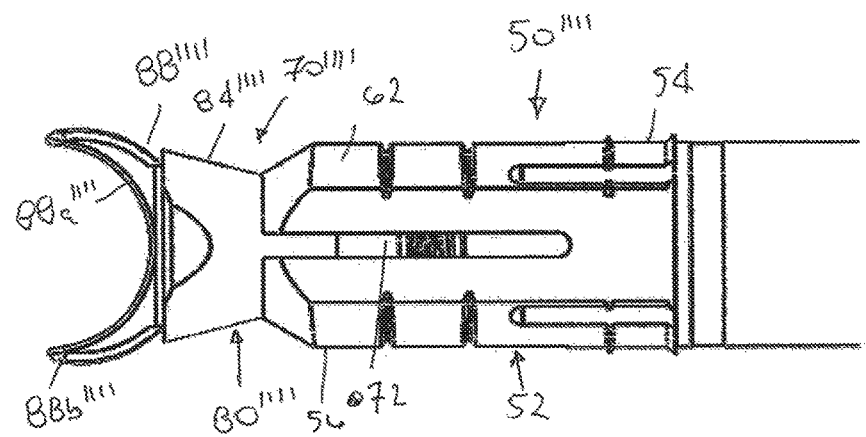
FIG. 16 is a side view of yet another embodiment of a tissue anchor carried on a distal end of a tool shaft.

Alternatively, the fork may define a width greater than the distal end 84 of the expander 80 and/or a greater height. For example, FIG. 16 shows another embodiment of an anchor 50'''' that includes a fork 88'''' in which the curved distal surface 88*a*'''' defines a larger radius and the tips 88*b*'''' may have longer lengths, e.g., to enhance capturing tissue between the tips 88*b*.''''

Figure 15A:
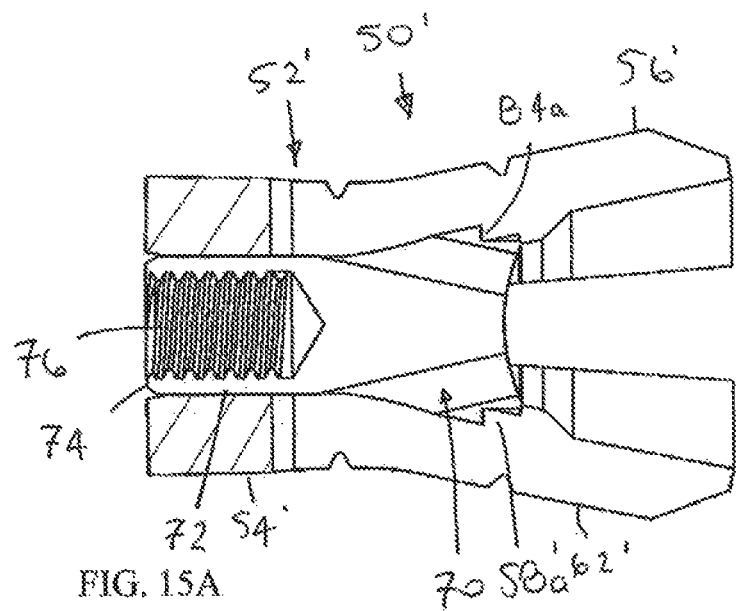
FIGS. 15A and 15B are cross-sectional and side views, respectively, of the tissue anchor of FIGS. 8-10 with the expander retracted to a proximal position to expand arms of the outer shell to an expanded configuration.

The outer shell 52 and expander 70 may include one or more features to limit movement of the expander 70 relative to the outer shell 52 during delivery and/or deployment. For example, the outer shell 52 may include one or more internal grooves, detents, or other features that may interact with corresponding features on the expander 70 to limit the expander 70 to moving between a distal or delivery position, e.g., as best seen in FIGS. 3 and 6, and proximal or deployed position, e.g., shown in FIGS. 15A-15C. For example, as shown in FIG. 6, the outer shell 52 includes an annular groove 58*a* extending circumferentially around the passage 58, and the proximal portion 74 of the expander 70 may include an annular step, ridge, or barb 74*a*, e.g., defining a ramped proximal edge and a blunt distal edge. The groove 58*a* and barb 74*a* may be located to initially secure the expander 70 in the distal position, i.e., with the proximal portion 72 disposed within the passage 58 and the ramped distal portion 80 extending distally from the outer shell 52. For example, the groove 58*a* and barb 74*a* may secure the expander 70 until the actuator is activated with sufficient force to direct the ridge 74*a* out of the groove 58*a*, e.g., during deployment of the anchor 50, as described further elsewhere herein. Alternatively, the groove 58*a* may be omitted and the barb 74*a* (and proximal portion 72) may be free to slide along the inside of the passage 58 between proximal and distal positions.

In addition, the barb 74*a* may be configured to pass over and engage a shoulder of the proximal end 54 of the outer shell 52. For example, as the expander 70 is retracted proximally, the barb 74*a* may exit the proximal end 54 of the outer shell 52 and expand outwardly such that subsequent distal movement engages the barb 74*a* to the proximal end 54 to prevent distal movement of the expander 70.

Figure 10:
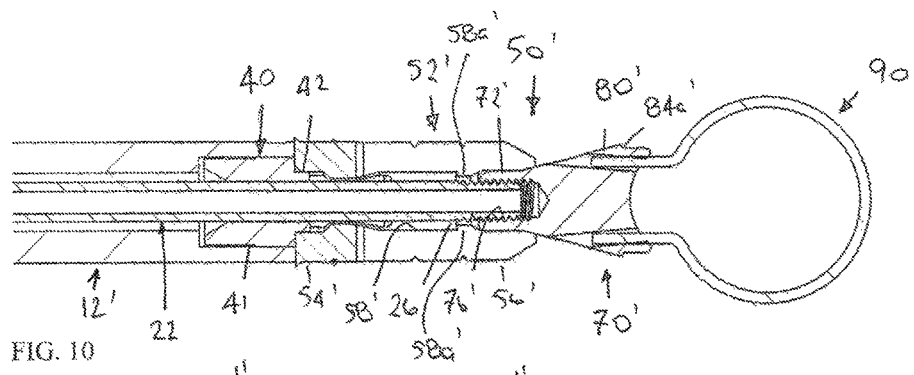
FIG. 10 is a cross-sectional view of the tissue anchor and shaft taken along plane 10-10 shown in FIG. 8.

In addition or alternatively, the distal end 84 may define a step or detent 84*a* that may be received in the groove 58*a* when the expander 70 is retracted into the passage 58 to the proximal position and the arms 62 are expanded, as described further below. For example, as shown in FIG. 10, the outer shell 52' may include one or more steps or tabs 58*a*' within the passage 58' over which one or more corresponding detents 84*a*' on the distal end 84 of the expander 70' may pass as the expander 70 is directed to the proximal position. The step(s) 58*a*' may have ramped proximal edge(s) that accommodate the distal end 84' moving proximally and blunt distal edge(s) that prevent the detent(s) 84*a*' from moving distally, thereby preventing distal movement of the expander 70.'

Figure 8:
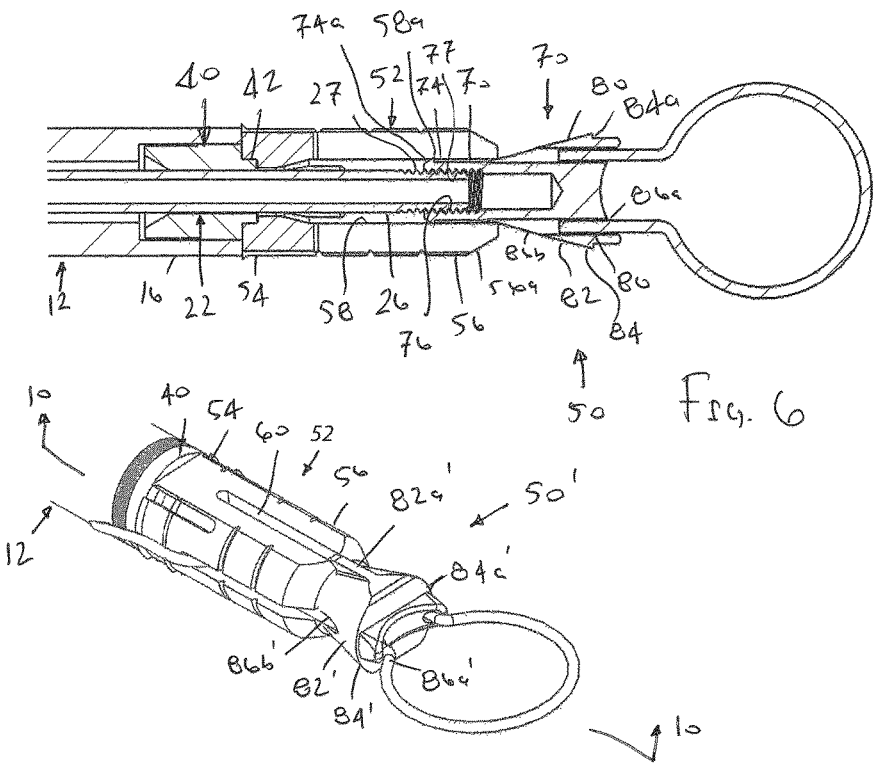
FIG. 8 is a perspective view of another embodiment of a tissue anchor carried on a distal end of a tool shaft.
Figure 9:
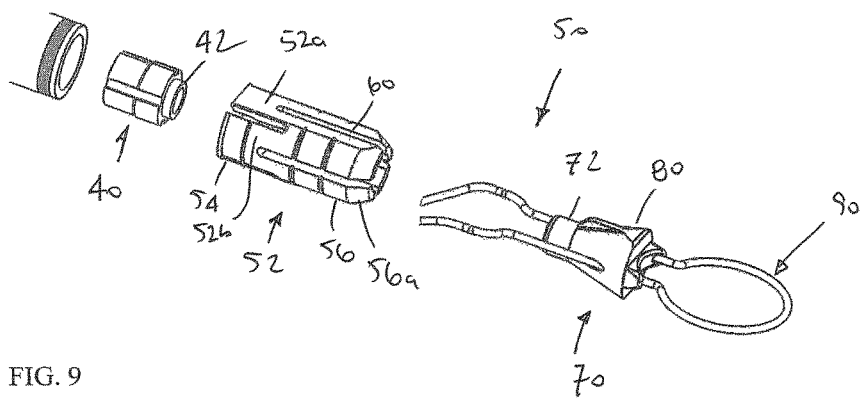
FIG. 9 is an exploded view of the tissue anchor of FIG. 8.

Optionally, the expander 70 and/or outer shell 52 may include cooperating features that allow axial movement while preventing rotation. For example, as shown in FIGS. 8 and 9, an embodiment of an anchor 50' is shown that includes an outer shell 52' and expander 70' generally similar to the embodiment shown in FIGS. 3-6. In this embodiment, the expander 70' includes one or more outwardly projecting tabs 82*a*' (e.g., two on opposite sides, one not shown) that may be slidably received within the distal slot(s) 60 in the outer shell 52 to accommodate axial movement while preventing rotation of the expander 70' relative to the outer shell 52.

Returning to FIGS. 3 and 4, the suture 90 may extend through the passages 86 in the expander 70 such that an intermediate region of the suture 90 defines a loop 92 distal to the fork 88, e.g., for capturing tissue, as described further below. First and second lengths 94 of the suture 90 may extend proximally from the passages 86 and be releasably secured to the handle 20 of the delivery tool 10, e.g., to cleat 20*g* (shown in FIGS. 1 and 2), as described further below. As can be seen in FIG. 3, the suture 90 may exit from the side openings 86*b* of the passages 86 and extend partially along the distal slots 60 in the outer shell 52, which may support the expander 70 relative to the outer shell 52, e.g., to minimize rotation of the expander 70 relative to the outer shell 52.

Figure 14A:
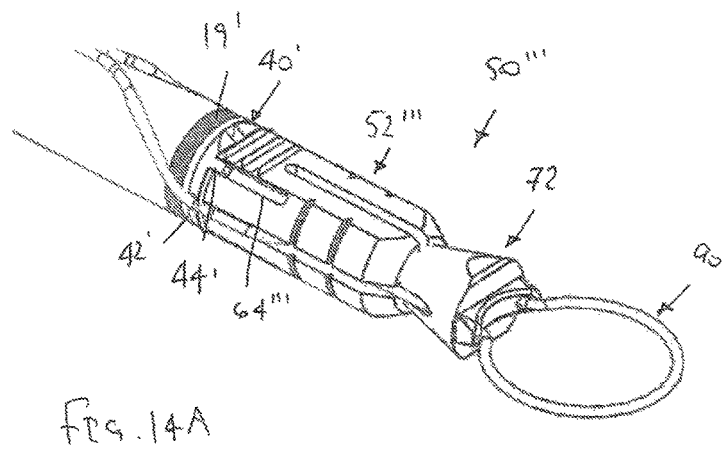
FIG. 14A is a perspective view of still another embodiment of a tissue anchor carried on a distal end of a tool shaft.
Figure 14B:
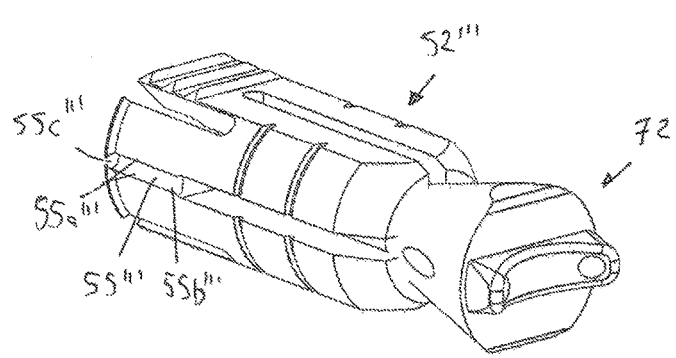
FIG. 14B is a perspective detail of an expandable outer shell of the tissue anchor of FIG. 14A showing suture grooves in a side surface of the outer shell.

Optionally, in any of the embodiments herein, the outer shell may include features to guide and/or restrict the suture 90 along the outer shell. For example, as shown in FIGS. 14 and 15, an outer shell 52''' may include grooves 55''' aligned with the distal slots 60 that may be sized to slidably receive the suture 90 therein, as shown in FIG. 15. As best seen in FIG. 14, the grooves 55''' may have a circular cross-section similar to the diameter of the suture 90, e.g., defining opposite edges 55*a*''' such that the inner surface 55*b*''' of the groove 55''' extends more than one hundred eight degrees (180°) of a circle between the edges 55*a*''' to an opening 55*c*.''' Thus, the suture 90 may be received in the groove 55''' by forcing the suture 90 through the opposite edges 55*a*''' of the groove 55''' or by sliding one end of the suture 90 into one end of the groove 55.''' Alternatively, the groove 55''' may define less than a one hundred eight degree (180°) arc, and a proximal opening 55*c*''' may be provided that allows the suture 90 to slide axially through the opening 55*c*''' but preventing the suture 90 from moving laterally out of the opening 55*c*.''' In this manner, the suture 90 may prevent the outer shell 52''' from rotating, while allowing relative axial movement.

Generally, with reference to FIGS. 3-6, during use, the anchor 50 may be delivered with the expander 70 in the distal position and the loop 92 disposed beyond the ramped distal portion 80, i.e., with the arms 62 of the outer shell 52 in their original, inner configuration. For example, as shown in FIGS. 7A-7H, the anchor 50 may be used to secure the end of a tendon 96 to a bone 98, e.g., when the tendon 96 has torn or otherwise separated from the bone 98.

Figure 2:
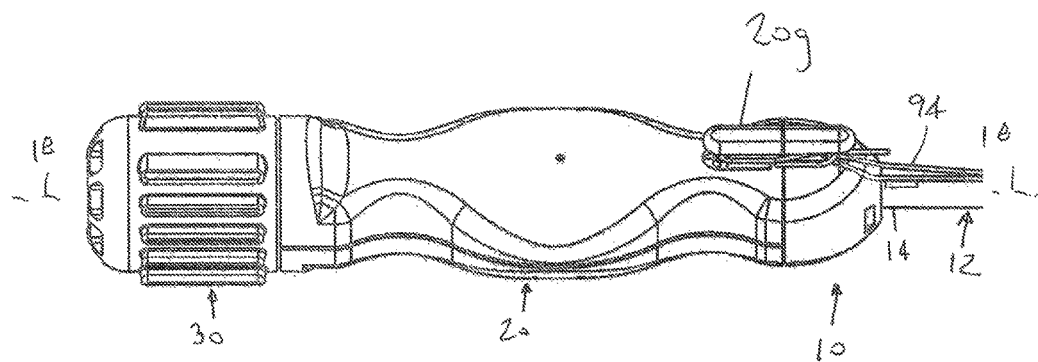
FIG. 2 is a detail of a handle for the tool shown in FIG. 1 showing a suture securing the tissue anchor to a distal end of the shaft.
Figure 7A:
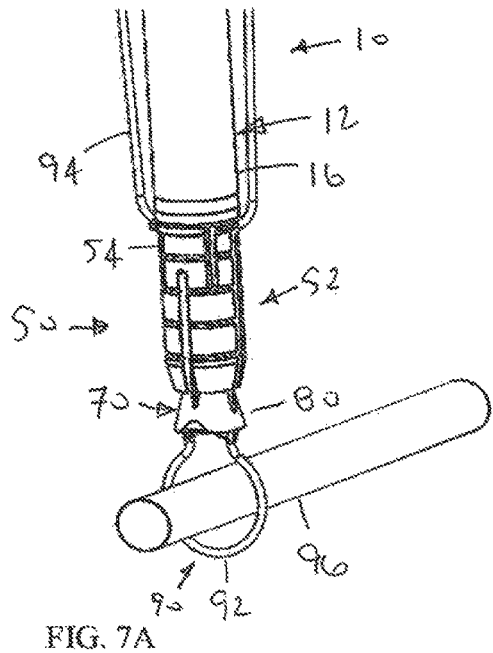
FIGS. 7A-7H show an exemplary method for securing a tendon to bone using the system of FIGS. 1-6.
Figure 7B:
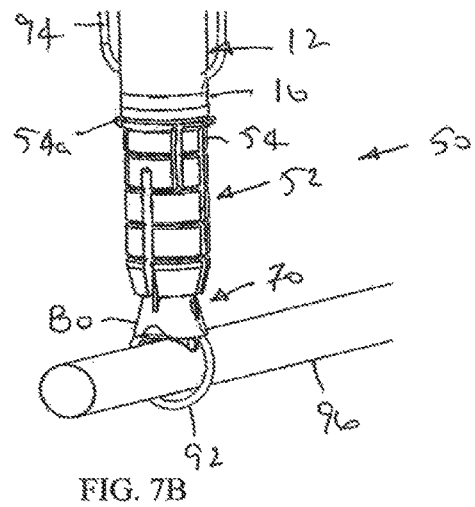
Figure 7C:
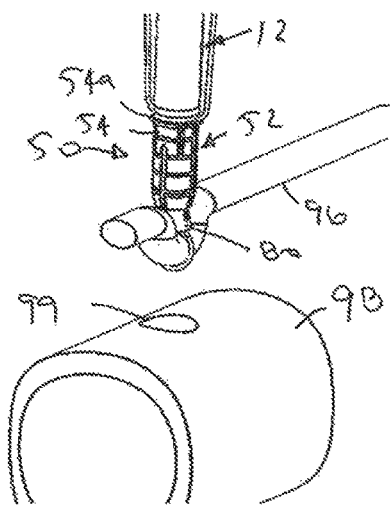
Figure 7D:
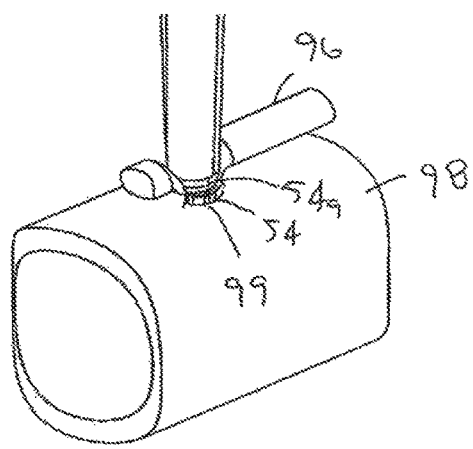
Figure 7E:
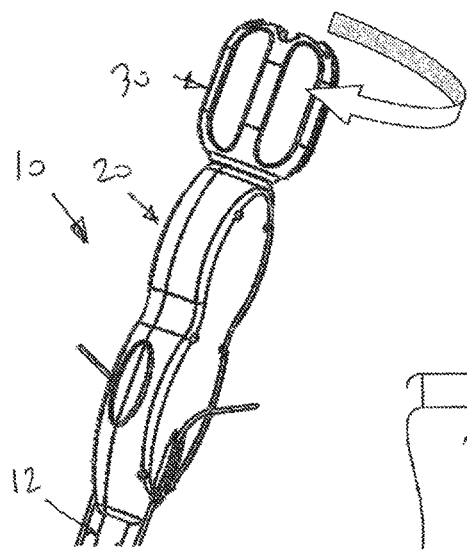

Initially, as shown in FIG. 7C, a bore 99 may be drilled into the bone 98 at a desired location using conventional methods. As shown in FIG. 7A, the tendon 96 may be inserted through the loop 92 and one or both of the ends 94 may be pulled to tighten the loop 92 around the tendon 96, as shown in FIG. 7B, and the ends 94 may be secured to the cleat 20g, e.g., as shown in FIG. 2. As shown in FIGS. 7C-7D, the loop 92 followed by the expander distal portion 80 and outer shell 52 may be inserted into the bore 99, thereby positioning the end of the tendon 96 at the bottom of the bore 99. For example, the bore 99 may be sized to receive the outer shell 52 and expander 70 in the delivery position e.g., having a diameter and/or depth to allow the anchor 50 to be fully inserted such that the proximal end 54 of the outer shell 52 is disposed within the bore 99 with the loop 92 and tissue pressed against the bottom of the bore 99, e.g., between the tips 88b of the fork 88. In an alternative embodiment, the anchor 50 may be used without the suture 90. For example, the tendon 96 may be guided into the bore 99 using the fork 88 without a suture, e.g., by placing the tendon 96 over the bore 99 and placing the tines 88b on either side of the tendon 96 and pressing the concave surface 88a against the tendon 96 to direct it into the bore 99.

Optionally, if the outer shell 52 includes a proximal flange 54a, the flange 54a may be seated against an outer surface of the bone 98, e.g., to stabilize the anchor 50. During insertion the tendon 96 may remain centered under the curved distal surface 88a of the fork 88 between the tips 88b, e.g., such that the fork 88 minimizes the possibility of the tendon 96 rolling off the side of the expander distal portion 80.

Figure 7F:
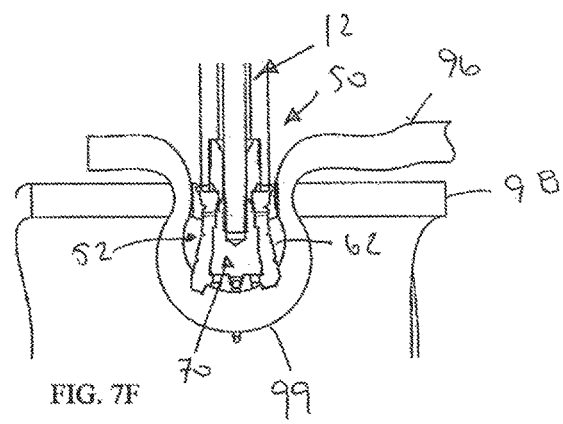
Figure 7G:
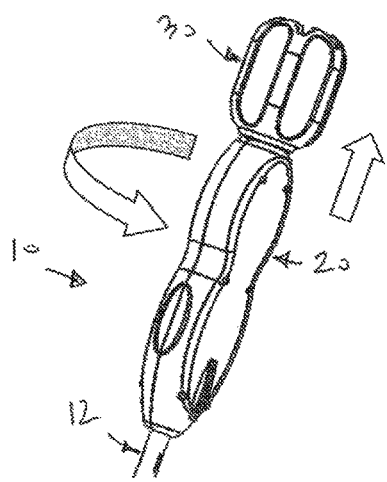
Figure 7H:
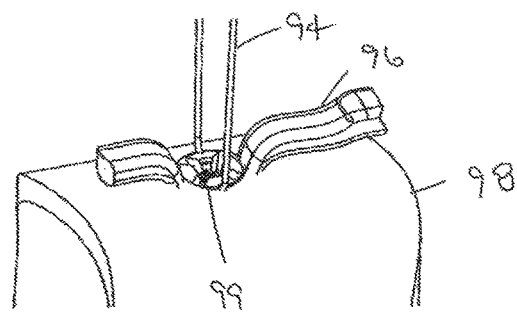

As the anchor 50 is inserted into the bore 99, the tendon 96 may fold over the planar surfaces 52a of the outer shell 52, e.g., as shown in FIG. 7F, thereby further retaining the tissue structure in a desired position and/or orientation. In addition, the planar surfaces 52a may allow a smaller bore to be used than if the outer shell 52 had a completely circular cross-section (which would require the bore to be much larger than the outer diameter of the outer shell to accommodate the tissue adjacent the outer shell 52). For example, the bore 99 may only require a diameter slightly larger than the rounded side surfaces 52b of the outer shell 52 (i.e., the overall outer diameter of the anchor 50) since the tendon 96 may be positioned in the space between the planar surfaces 52a and the inner surface of the bore 99.

Figure 15B:
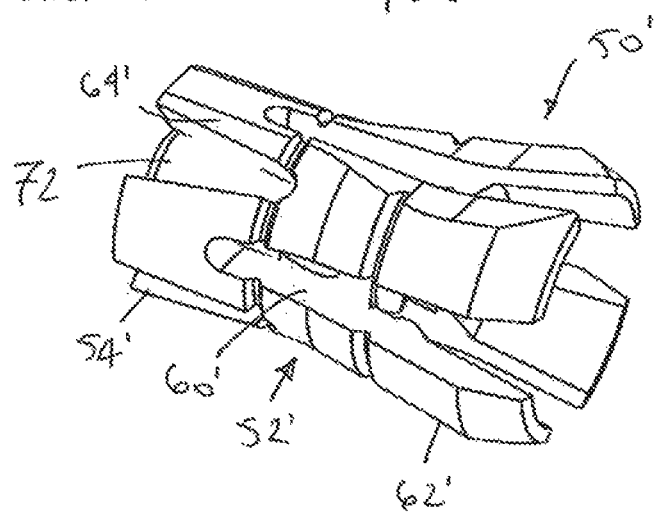
Figure 15C:
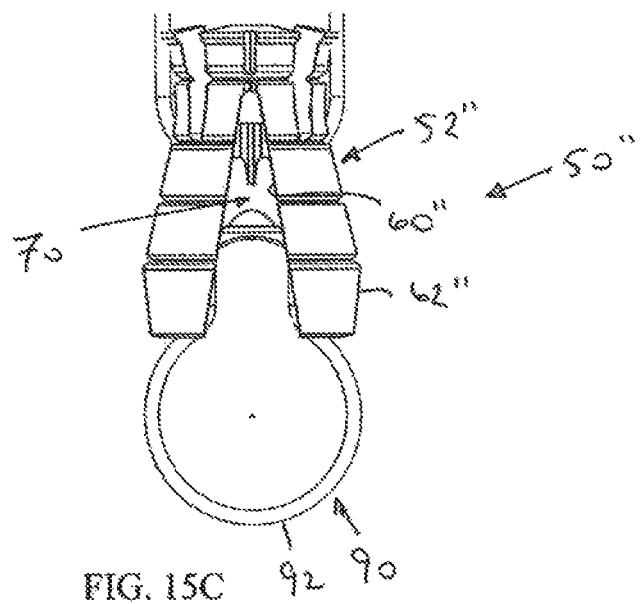
FIG. 15C is a side view of the tissue anchor of FIGS. 11-13 with the expander retracted to a proximal position to expand arms of the outer shell to an expanded configuration.

Once the anchor 50 and tissue structure are properly received in the bore, the expander 70 may be retracted proximally to expand the outer shell 52, e.g., using an actuator, such as the actuator 30 on the delivery tool 10 shown in FIGS. 1-2 or other embodiments, as described further elsewhere herein. For example, as shown in FIGS. 7F and 15A-15C, as the distal portion 80 of the expander 70 is pulled into the passage 58, the ramped outer surface 82 causes the arms 62 to deform outwardly towards an expanded configuration, thereby engaging the arms 62 into the surrounded bone 98 and securing the anchor 50. The expander 70 may be retracted to the distal or deployed position, e.g., until the detent(s) 84a pass over and/or otherwise engage with the corresponding features on the outer shell 52 within the passage 58, thereby preventing the expander 70 from subsequently moving distally back towards the delivery position and locking the arms 62 in the expanded configuration, e.g., as shown in FIG. 15C. In addition, if the outer shell 52 includes proximal slots 64, the proximal end 54 may flare outwardly relative to a central region of the outer shell 52, as the expander 70 is retracted, e.g., as shown in FIG. 15B, to further engage the bone 98, e.g., to engage into cortical bone and further secure the anchor 50.

Figure 24:
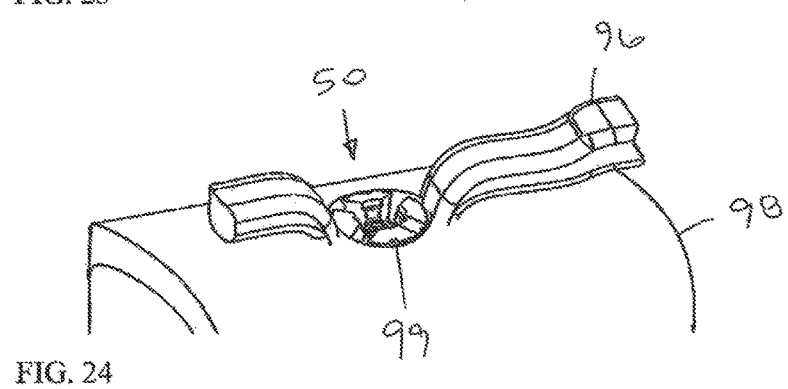
FIG. 24 is a detail showing an exemplary embodiment of an anchor securing a tendon to a bone.

Once the anchor 50 is fully expanded, the ends 94 of the suture 90 may be released from the handle 20, and the anchor 50 disengaged from the tool 10, as described further below. Optionally, one or more knots (not shown) may be created using the ends 94 of the suture 90 and directed down against the proximal end 54 of the outer shell 52, e.g., to capture additional tissue and/or further secure the anchor 50 relative to the bone 98. Any excess suture 90 may be cut or otherwise separated, as desired, thereby implanting the anchor 50 within the bore 99 and securing the end of the tendon 96, e.g., as shown in FIG. 24.

Figure 17:
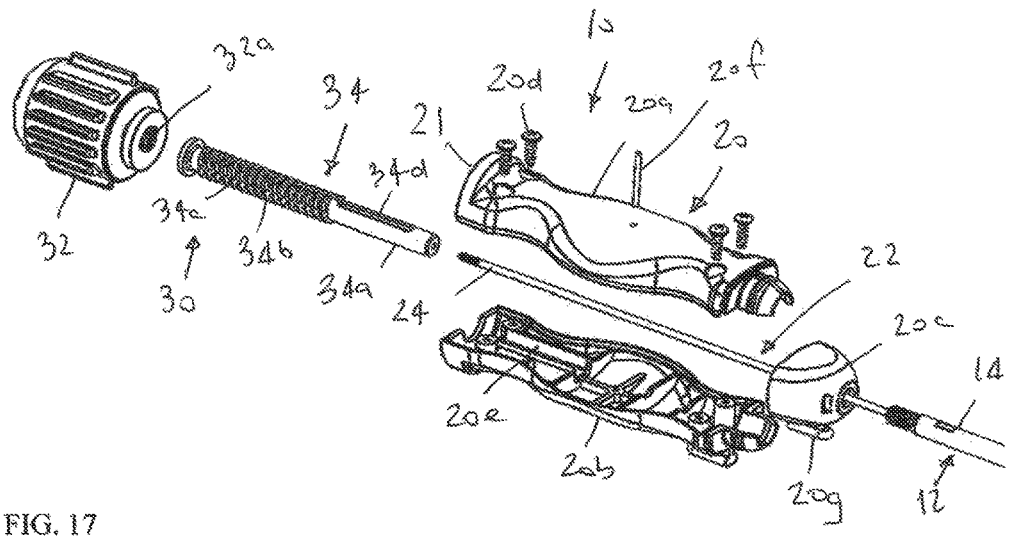
FIG. 17 is an exploded view of the handle of the delivery tool of FIGS. 1 and 2.

For example, turning to FIG. 17, an exemplary embodiment of a handle 20 and actuator 30 are shown that may be included in the tool 10 shown in FIGS. 1 and 2. Generally, the handle 20 includes one or more outer housing components, e.g., clamshells or halves 20a, 20b, and end cap 20c, that may be fabricated separately and assembled together to provide an outer housing containing internal components and provide a desired shape to facilitate manipulation and use of the tool 10. In an exemplary embodiment, a plurality of screws 20d and/or other connectors, e.g., detents, press fit pins, tabs, and the like, may be used to secure the halves 20a, 20b together and substantially permanently attach the end cap 20c to the halves 20a, 20b. In addition or alternatively, the components of the handle may be formed as more or fewer pieces and/or may be assembled using one or more of bonding with adhesive, sonic welding, and the like.

The proximal end 14 of the outer shaft 12 may be attached to the handle 20, e.g., to end cap 20c, by one or more of mating threads, interference fit, bonding with adhesive, sonic welding, and the like, e.g., such that the handle 20 and outer shaft 12 define a central longitudinal axis 18 for the tool 10. The inner shaft 22 may be coaxially positioned within the outer shaft 12, e.g., such that the proximal end 24 is disposed within the handle 20 proximal to the outer shaft proximal end 14, as shown in FIG. 17, and the distal end 26 extends beyond the outer shaft distal end 16, as shown in FIG. 4.

In addition, the end cap 20c (or alternatively, one of the halves 20a, 20b) includes a cleat 20g for securing the ends 94 of the suture 90 to the handle 20, e.g., during delivery and expansion of the anchor 50. For example, once an anchor 50 has been coupled to and/or positioned adjacent the distal ends 16, 26 of the outer and inner shafts 12, 22, the suture ends 94 may be pulled and placed adjacent the outer shaft 12 and then wrapped one or more times around the cleat 20g. Once the anchor 50 is delivered and deployed, as described elsewhere herein, the ends 94 may be unwound before the tool 10 is removed.

With continued reference to FIG. 17, the actuator 30 generally includes an actuator member, e.g., rotatable knob 32 that may be manipulated by the user, and an actuator shaft 34 coupled to knob 32 and the proximal end 24 of the inner shaft 22. For example, as shown in FIGS. 1 and 2, the knob 32 may be mounted on a proximal end 21 of the handle 20 such that the knob 32 is free to rotate, although it will be appreciated that the knob 32 may be located at an intermediate or other location on the handle 20 (not shown), if desired, as long as the knob 32 is coupled to the actuator shaft 34. A distal end 34a of the actuator shaft 34 may be coupled to the proximal end 24 of the inner shaft 22, e.g., by one or more of cooperating threads, interference fit, bonding with adhesive, sonic welding, and the like. The actuator shaft 34 may be mounted within the handle 20 such that rotation of the knob 32 causes the actuator shaft 34 to move axially, e.g., proximally, to direct the inner shaft 22 axially relative to the outer shaft 12.

For example, the actuator shaft 34 may include a threaded portion 34b and the knob 32 may include a threaded opening and/or passage 32a that cooperate to cause the threaded portion 34b of the actuator shaft 34 to move axially into and/or through the knob 32 as the knob 32 is rotated. The actuator shaft 34 also includes flat regions or other features 34c and one or both halves 20a, 20b may include a track or other guide 20e that cooperate with the features 34c to allow the actuator shaft 34 to move axially without rotation. Thus, rotation of the knob 32 causes the threaded region 34b to move proximally into or through the opening 32a in the knob 32, while the flat regions 34c slide along the track 20e, thereby retracting the distal end 26 of the inner shaft 22 relative to the outer shaft 12 to direct the expander 70 from the distal position to the proximal position.

Optionally, a pin 20f or other stop may be provided in the handle 20 to limit movement of the actuator shaft 34, e.g., to limit retraction of the inner shaft 22. For example, as shown in FIG. 17, a pin 20f may be mounted across the halves 20a, 20b at a predetermined location and be received through a slot 34d in the actuator shaft 34. Thus, as the actuator shaft 34 is retracted, the pin 20f may move along the slot 34d until it reaches the end of the slot 34d, thereby preventing further retraction of the actuator shaft 34 and inner shaft 22. For example, once the anchor 50 is inserted into a bore, the knob 32 may be rotated to retract the actuator shaft 34, inner shaft 22, and expander 70 to expand the arms 62 of the outer shell 52 to engage adjacent bone, thereby securing the anchor 50 to the bone, as described above.

Once the anchor 50 is fully expanded, the suture ends 94 may be removed from the cleat 20g, and the entire tool 10 rotated to unthread the inner shaft 22 from the expander 70. Alternatively, the knob 32 may be rotated further, e.g., if the pin 20f is omitted or positioned to accommodate additional retraction of the actuator shaft 34, to cause the inner shaft 22 to retract further. The threads 77 in the expander 70 and/or the threads 27 on the distal end 26 of the inner shaft 22 may be configured to strip and/or otherwise fail when subjected to additional force to strip the threads 77, 27 and allow the inner shaft 22 to be retracted to remove the distal end 26 and release the anchor 50 from the tool 10.

Figure 18A:
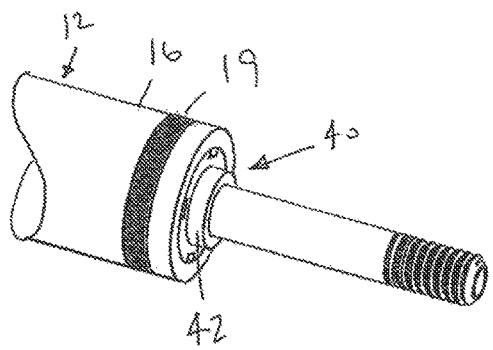
FIGS. 18A and 18B are details showing an example of an interface for coupling a tissue anchor, such as the tissue anchor of FIGS. 3-7 to the shaft of a delivery tool, such as the delivery tool of FIGS. 1 and 2.
Figure 18B:
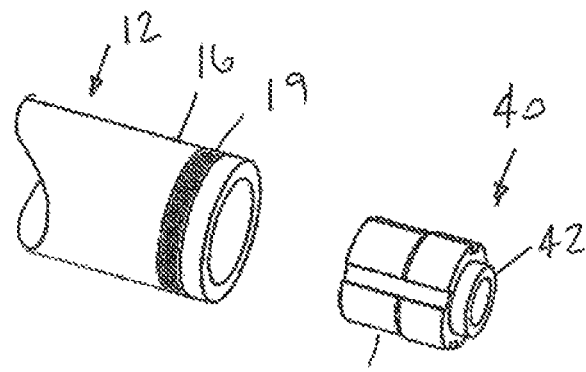

Optionally, an interface or end cap 40 may be provided adjacent the distal end 16 of the outer shaft 12 to couple and/or limit movement of the outer shell 52 of the anchor 50 relative to the outer shaft 12. For example, as shown in FIGS. 18A and 18B, an exemplary embodiment of an end cap 40 is shown that includes an insertion body 41 that may be received within a recess in the distal end 16 of the outer shaft 12, e.g., around the inner shaft 22. The insertion body 41 may be secured within the distal end 16, e.g., by one or more of press fit, bonding with adhesive, and the like, such that an annular sleeve 42 extends from the distal end 16 of the outer shaft 12. The annular sleeve 42 may be sized to be received within the proximal end 54 of the outer shell 52, e.g., as shown in FIGS. 3 and 7, to support the proximal end 54 during delivery and deployment of the anchor 50. For example, the end cap 40 may be formed from metal, e.g., stainless steel, plastic, e.g., ABS, and the like, that are substantially rigid to support the proximal end 54, e.g., to prevent collapse or misalignment of the proximal end 54 during expansion of the arms 62.

Figure 12:
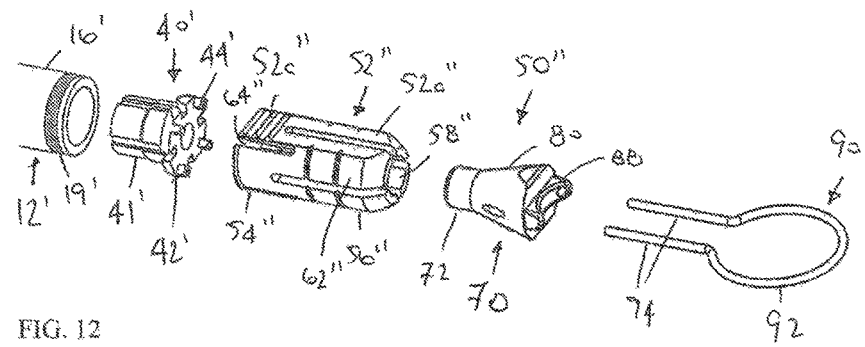
FIG. 12 is an exploded view of the tissue anchor of FIG. 11.
Figure 13:
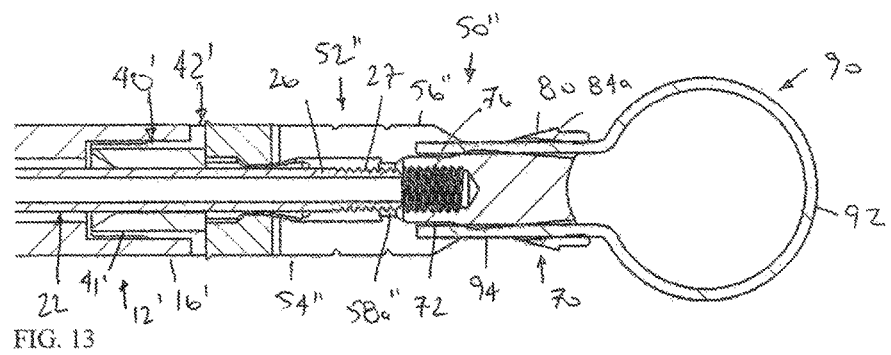
FIG. 13 is a cross-sectional view of the tissue anchor and shaft taken along plane 13-13 shown in FIG. 11.
Figure 19A:
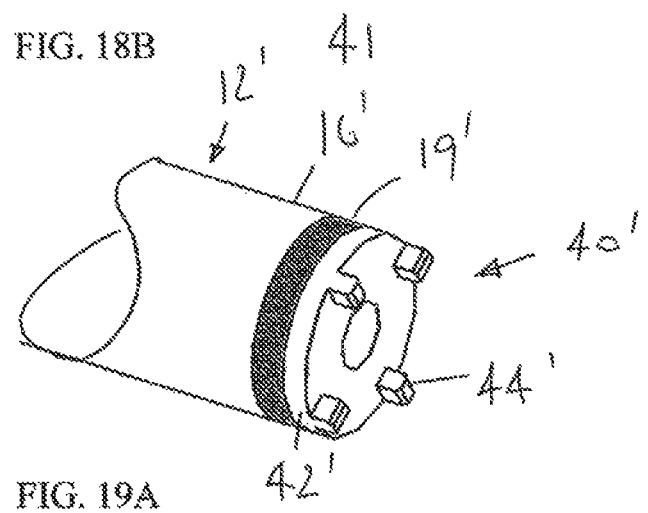
FIGS. 19A and 19B are details showing another example of an interface for coupling a tissue anchor to a delivery tool, such as that shown in FIGS. 11-13.
Figure 19B:
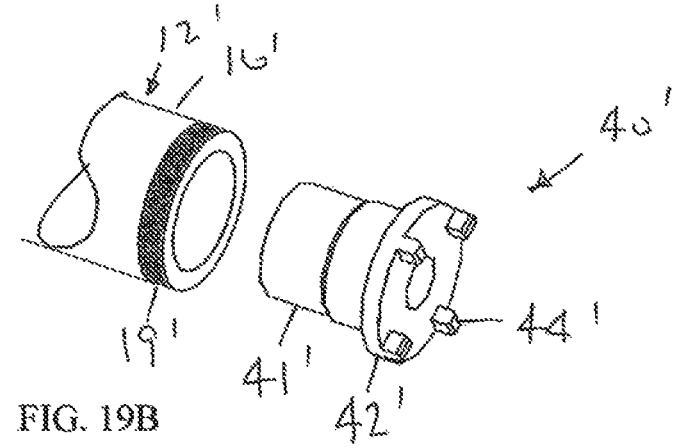

Alternatively, as shown in FIGS. 19A and 19B, another embodiment of an interface or end cap 40' is shown that includes an insertion body 41' sized to be received within the distal end 16' of the outer shaft 12' such that a disc 42' is disposed adjacent the distal end 16,' e.g., as shown in FIGS. 11-13. The disc 42' includes one or more tabs 44' sized to be received within proximal slots 64" in the outer shell 52," e.g., four tabs 44' received in respective slots 64." In this embodiment, the tabs 44' may maintain the outer shell 52" is a desired angular orientation on the outer shaft 12, e.g., preventing the outer shell 52" from rotating relative to the outer shaft 12' and/or otherwise stabilizing the anchor 50" on the shaft 12,' e.g., during delivery and deployment.

Turning to FIGS. 20A and 20B, an alternative embodiment of an outer shaft 12" is shown that may facilitate delivery of relatively smaller anchors. As shown, the distal end 16" of the outer shaft 12" includes a transition 17" from a main diameter of the outer shaft 12" to a reduced diameter tip. The tip may receive an end cap 40" similar to the end caps described previously. Optionally, in any of the embodiments herein, the outer shaft 12" may include a marker 19," at the tip of the distal end 16" or another predetermined location along the outer shaft 12." The marker 19" may provide a visual indication to the user, e.g., to facilitate delivery and/or positioning the anchor 150 within a bore (not shown).

Figure 21:
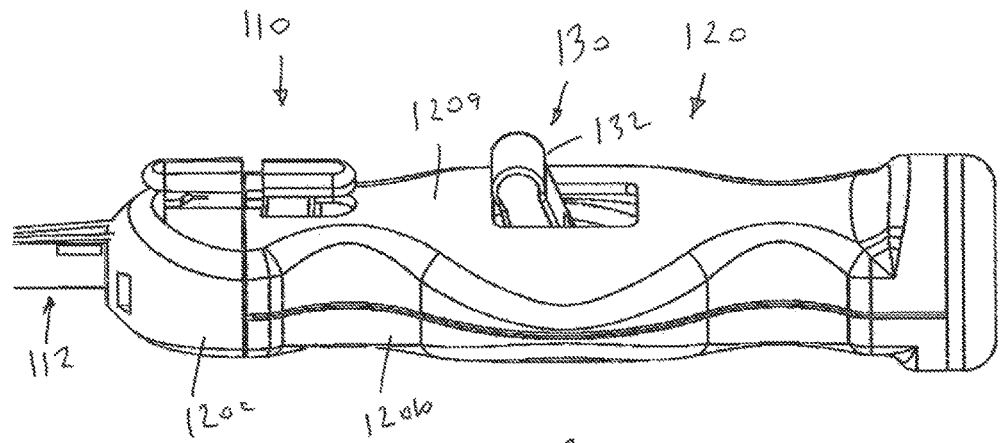
FIG. 21 is a side view of another embodiment of a handle and actuator that may be provided on a delivery tool.
Figure 22A:
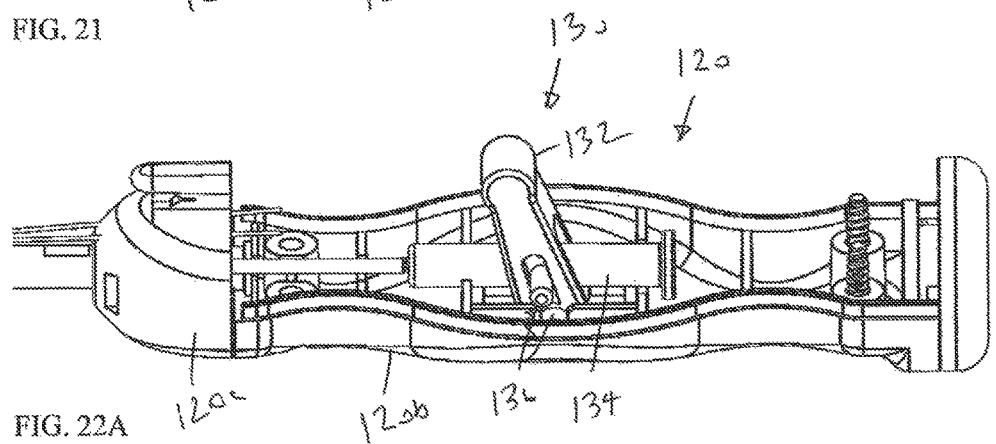
FIGS. 22A and 22B are perspective views of the handle of FIG. 21 with a cover removed and the actuator in advanced and retracted positions, respectively.
Figure 22B:
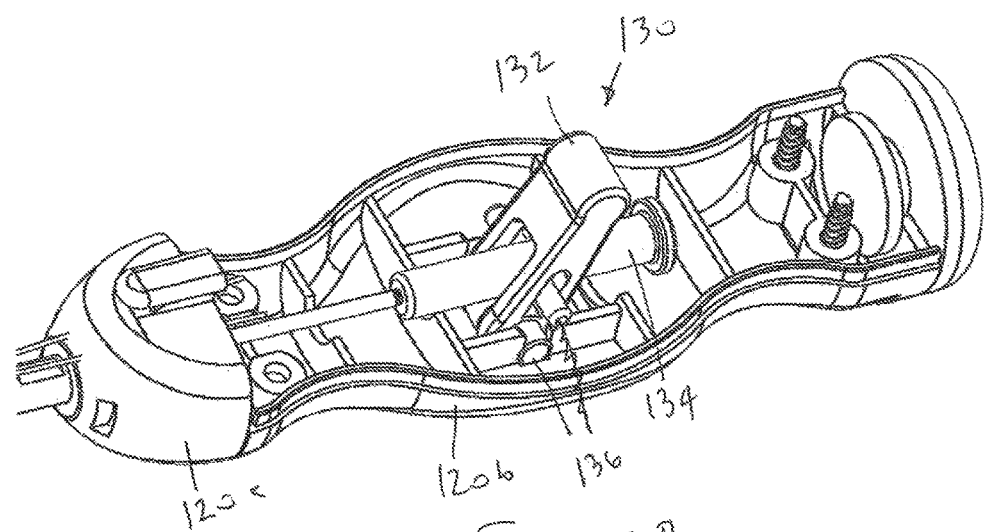
Figure 23:
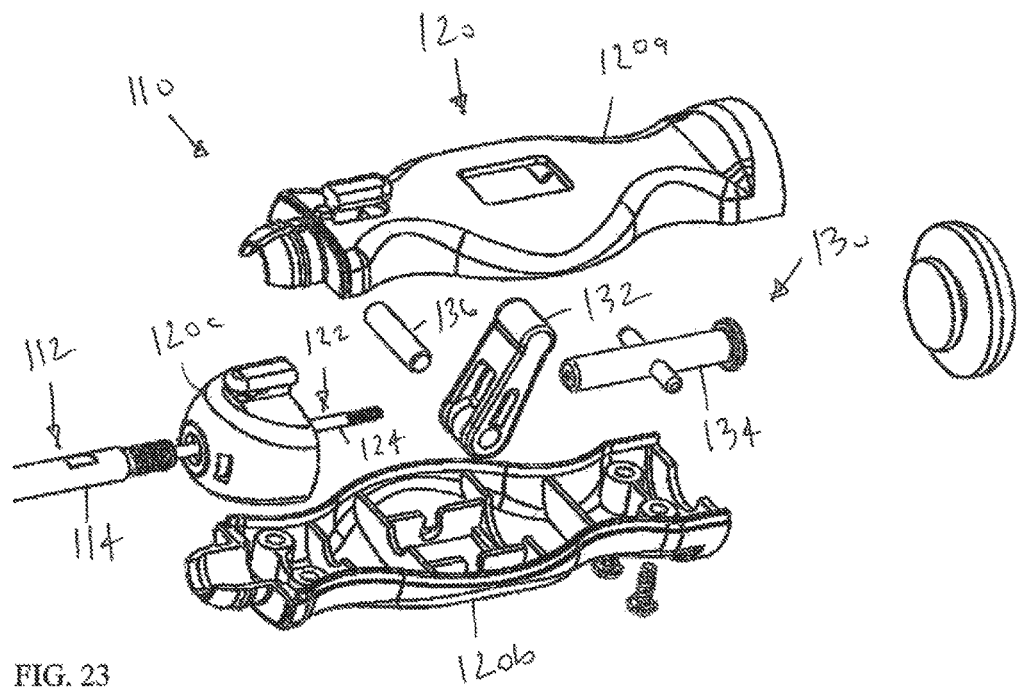
FIG. 23 is an exploded view of the handle of FIG. 21.

Turning to FIGS. 21-23, another embodiment of a delivery tool 110 and handle 120 is shown that may be used to deploy a tissue anchor (not shown), such as any of the embodiments described herein. Generally, the housing 120 includes one or more outer housing components, e.g., clamshells 120a, 120b, end cap 120c, and the like, similar to the previous embodiments. As shown, a proximal end 114 of an outer shaft 112 coupled to the end cap 120c, which may carry a suture cleat 120g, also similar to the previous embodiments.

In addition, an actuator 130 is provided on the handle 120, which may be coupled to an inner shaft 122 that is, in turn, coupled to an expander of the tissue anchor (not shown). Unlike the previous embodiments, the actuator 130 includes a lever 132 pivotally mounted to the handle 120 at axle 136 such that the lever 132 may be directed between an advanced position, e.g., as shown in FIGS. 21 and 22A and a retracted position, e.g., as shown in FIGS. 22B and 23.

The inner shaft 122 may be coaxially positioned within the outer shaft 112, e.g., such that the proximal end 124 is disposed within the handle 20 and coupled to the lever 132, and the distal end (not shown) extends beyond the outer shaft distal end (also not shown), similar to the previous embodiments. For example, an actuator shaft 134 may be coupled to the lever 132 and to the proximal end 124 of the inner shaft such that movement of the lever 132 from the advanced position to the retracted position causes the actuator shaft 134 and inner shaft 122 to move proximally, e.g., to retracted the expander of the tissue anchor (not shown), similar to other embodiments described herein.

One of the advantages of the tissue anchors described herein is that they may be reversible, e.g., the arms of the outer shell may be collapsed at least partially towards their original, delivery configuration, e.g., if it is desired or necessary to remove a tissue anchor after delivery and deployment. For example, as shown in FIGS. 25A-25E, a delivery tool, such as the tool 10 shown in FIGS. 1-2, may be used to remove the anchor 50 (which may be any of the embodiments described herein). In the embodiment shown, the threads 77 of the expander 70 remain intact after the outer shell 52 was expanded, e.g., by unthreading the inner shaft of the delivery tool (not shown) after deployment, as described above.

Figure 25A:
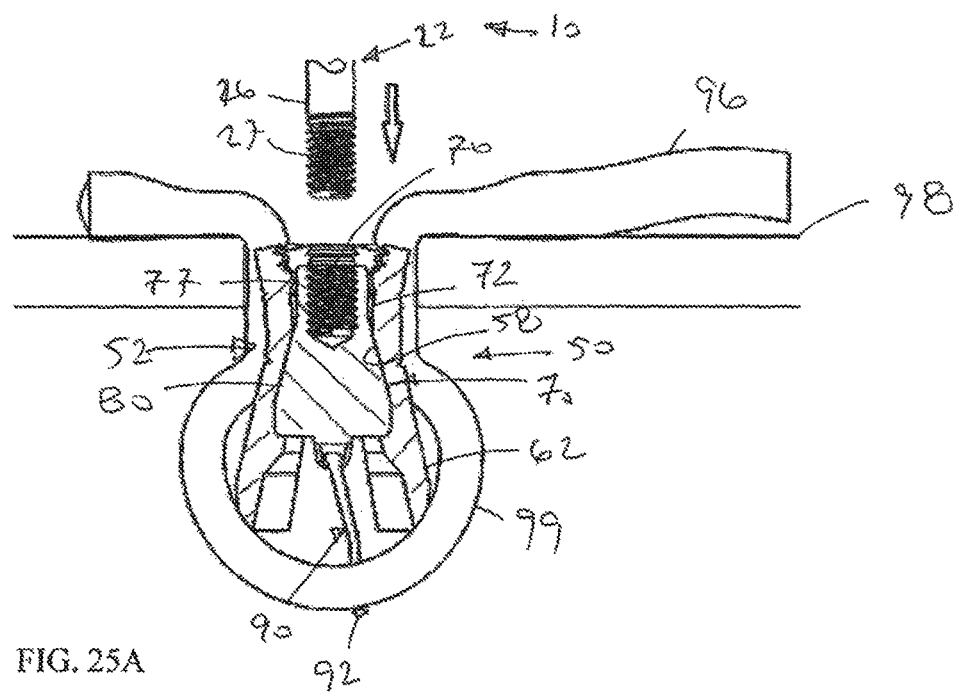
FIGS. 25A-25E show an exemplary method for removing a tissue anchor implanted into a bone, e.g., using the delivery tool of FIGS. 1 and 2.
Figure 25B:
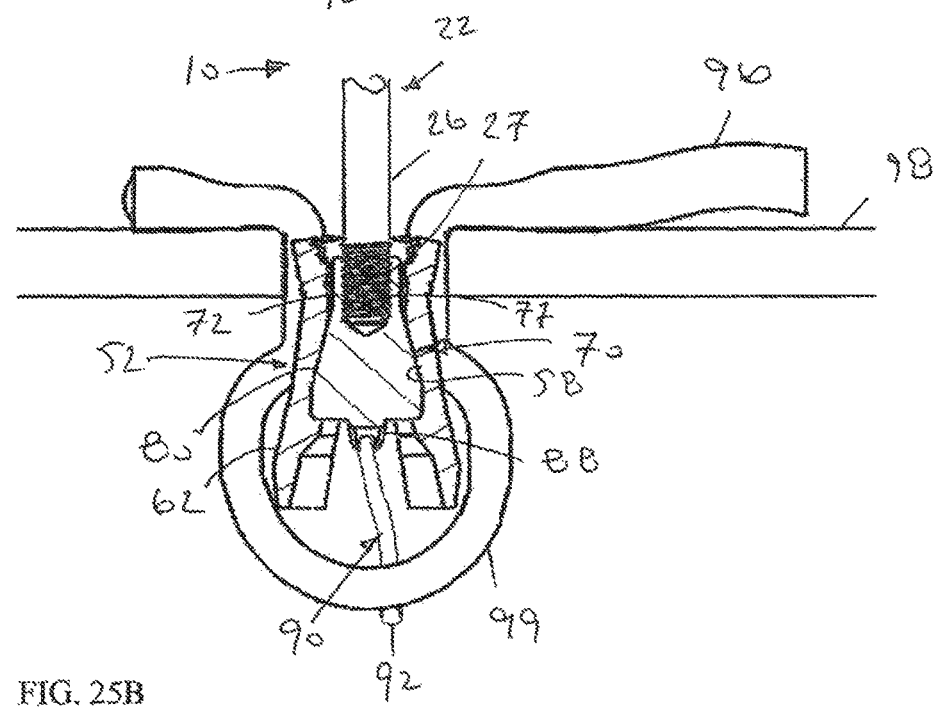
Figure 25C:
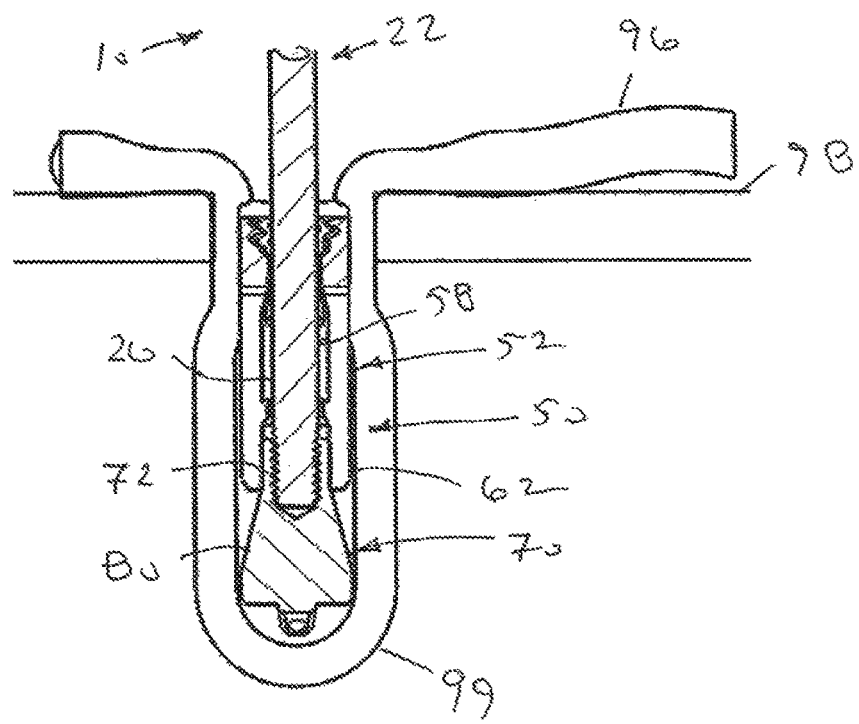
Figure 25D:
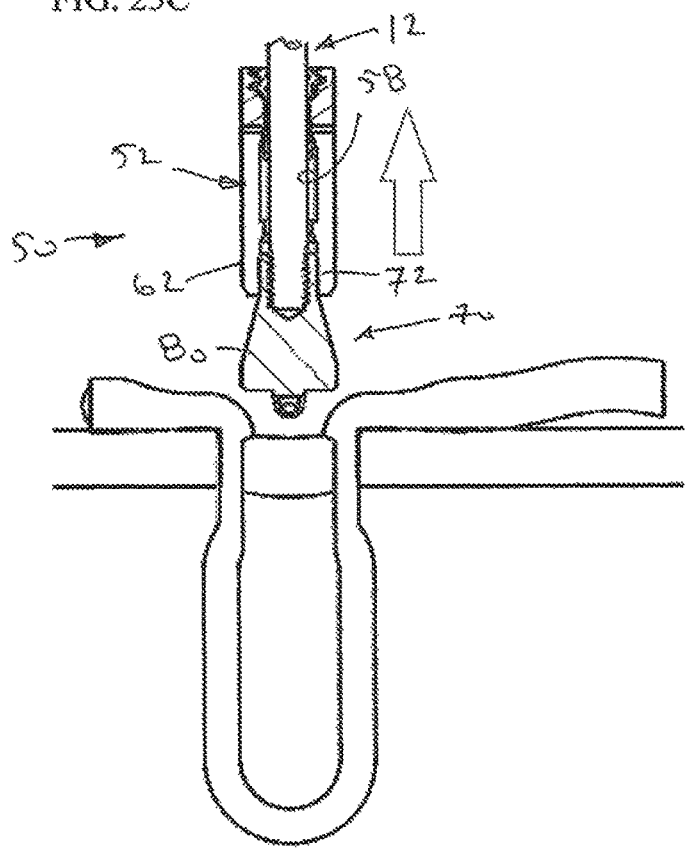
Figure 25E:
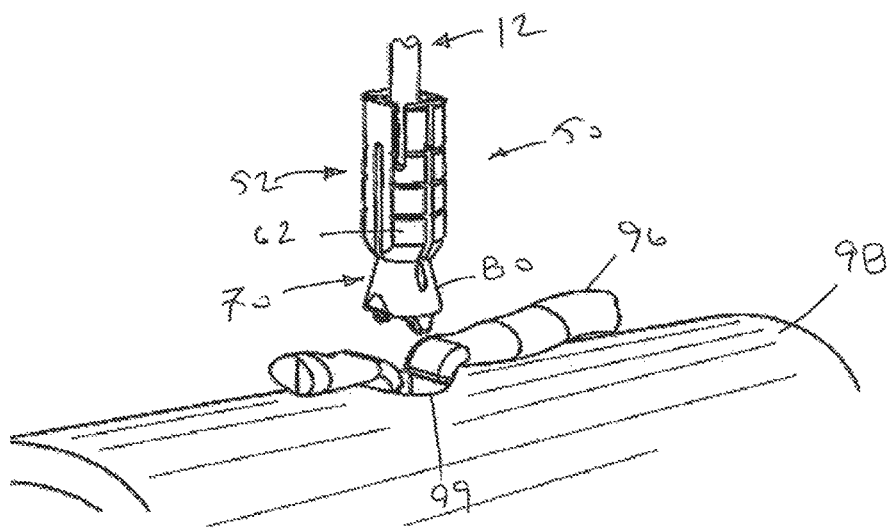

To retrieve the anchor 50, the inner shaft 22 of the tool 10 being used, may be advanced, e.g., by reversing the actuator (not shown), to provide clearance of the threads 27 beyond the distal end 16 of the outer shaft 12. As shown in FIGS. 25A and 25B, the distal end 26 of the inner shaft 22 may then be inserted into the recess 76 and then the entire tool 10 may be rotated to thread the threads 27 on the distal end 26 with the threads 77 in the recess 76. Once the threads 27, 77 are sufficiently engaged, the distal end 26 (e.g., the entire tool 10 or only the inner shaft 22) may be advanced to direct the expander 70 distally, thereby moving the ramped distal portion 80 out of the passage 58 in the outer shell 52 until the arms 62 are free to collapse. For example, a mallet or other tool (not shown) may be used to tap the handle 20 to force the expander 70 out of the outer shell 52. In one embodiment, the arms 62 may be resiliently biased to return at least partially inwardly to disengage the surrounding bone 98, e.g., as shown in FIG. 25C, whereupon the entire inner shaft 22/tool 10 may be withdrawn proximally (without rotation), thereby removing the entire anchor 50 from the bore 99, as shown in FIGS. 25D and 25E. Alternatively, if the arms 62 do not automatically collapse inwardly, proximal movement of the inner shaft 22/tool 10 may pull the entire anchor 50 proximally, thereby disengaging the arms 62 from the bone 98 and allowing the anchor 50 to be removed. If desired, the tool 10, coupled to the anchor 50, may be pivoted or otherwise moved laterally to facilitate disengaging the arms 52 from the bone 98 before removal of the anchor 50. In another alternative, a forceps or other tool (not shown) may be used to pull the outer shell 52 proximally and/or laterally to disengage the anchor 50 from the bone 98 and allow removal.

Figure 26:
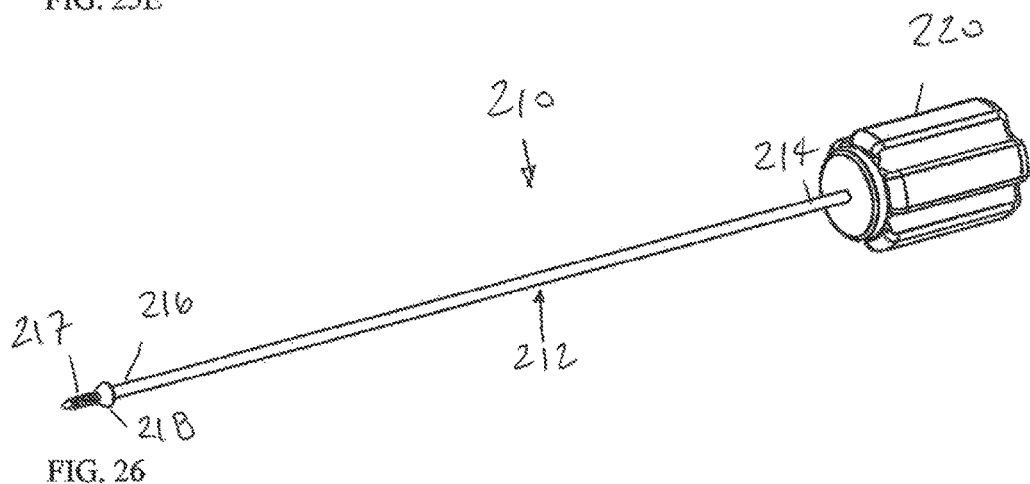
FIG. 26 is a perspective view of an exemplary embodiment of a removal tool for removing a tissue anchor implanted into a bone.
Figure 27:
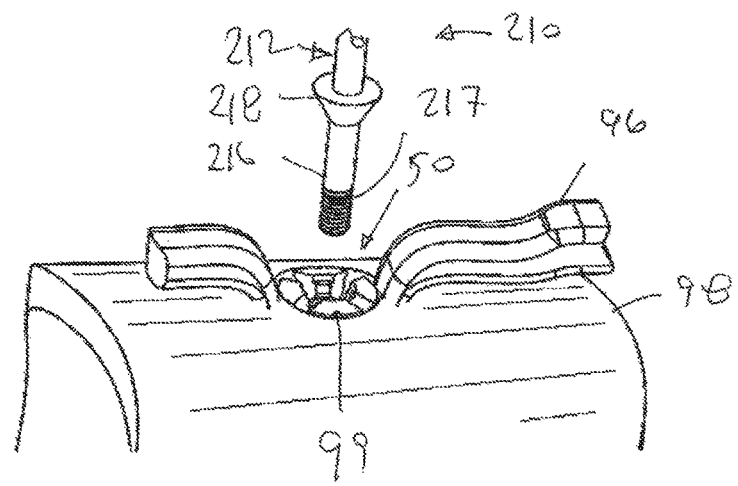
FIG. 27 is a detail showing an exemplary method for removing a tissue anchor implanted into a bone using the removal tool of FIG. 26.

Turning to FIG. 26, an exemplary embodiment of a specialized removal tool 210 is shown that may be used to remove a tissue anchor 50, e.g., as shown in FIG. 27. The tool 210 includes an elongate, rigid shaft 212 including a proximal end 214 carrying a handle 220 and a distal end 216 including one or more threads 217. In addition, the shaft 212 may include a ramped stop member 218 spaced apart from the threads 217, e.g., defining a tapered distal surface 218a and a blunt proximal surface 218b.

Figure 28:
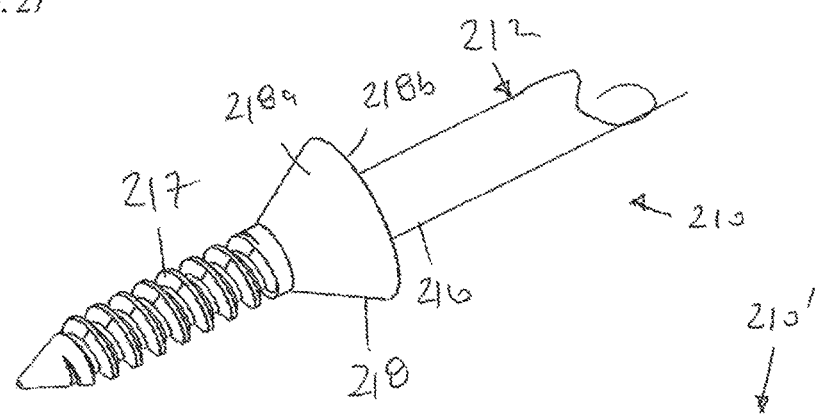
FIG. 28 is a detail showing an exemplary embodiment of a tip that may be provided on the removal tool of FIG. 26.
Figure 29A:
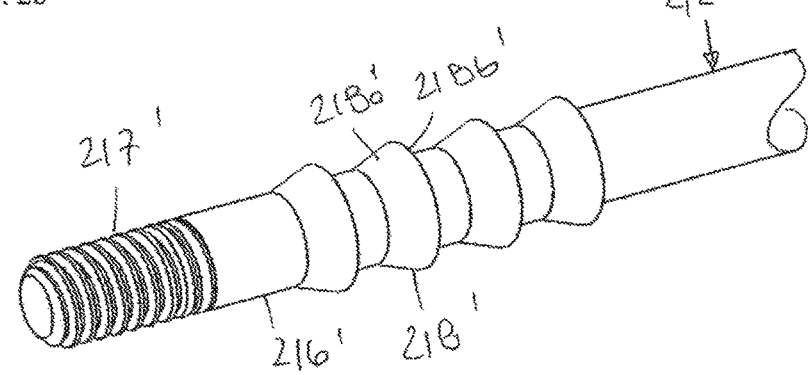
FIGS. 29A and 29B are details of alternative embodiments of tips that may be provided on a removal tool.
Figure 29B:
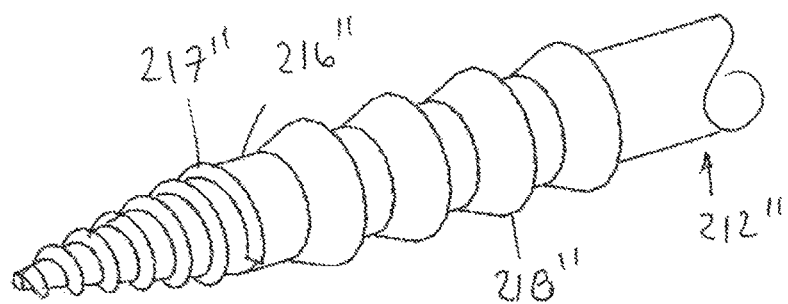

For example, as shown in FIG. 28, the threads 217 may be self-tapping, e.g., such that, if the threads 77 of the expander 70 were stripped when the delivery tool (not shown) was removed, the threads 217 may allow the distal end 216 to be threaded directly into the recess 76 of the expander 70. Thus, the distal end 216 may be threaded directly into the recess 76, thereby creating new threads in the expander 70, e.g., until the stop member 218 engages the proximal end 54 of the outer shell 52. Alternatively, the threads 217 may match the original threads of the expander 70, e.g., if the threads are still intact after the anchor 50 was implanted. For example, FIG. 29A shows an alternative embodiment where the distal end 216' includes uniform threads 217' matching the original threads in the expander 70. In a further alternative, FIG. 29B shows another example of threads 217" that may be provided that may more easily locate the passage 76 in the expander 70 and/or allow easier thread engagement for a larger range of diameters. For example, in this alternative, the tip may include a rounded and/or tapered unthreaded portion that may be guided easily into the recess 76 and relatively deep threads 217" that may bite into a broad range of diameters for the recess 76.

Returning to FIG. 28, the stop member 218 may be seated at least partially within the proximal end 54 of the outer shell 52, e.g., to stabilize the anchor 50. Once threaded sufficiently, the tool 210 may be advanced to push the expander 70 distally out of the outer shell 52, similar to the previous embodiment. Once the expander 70 is advanced out of the outer shell 52, the arms (not shown) may be collapsed and/or otherwise allow the anchor 50 to be removed. Optionally, the tool 210 may be directed laterally to facilitate disengaging the arms 62 before removing the anchor 50.

Figure 30:
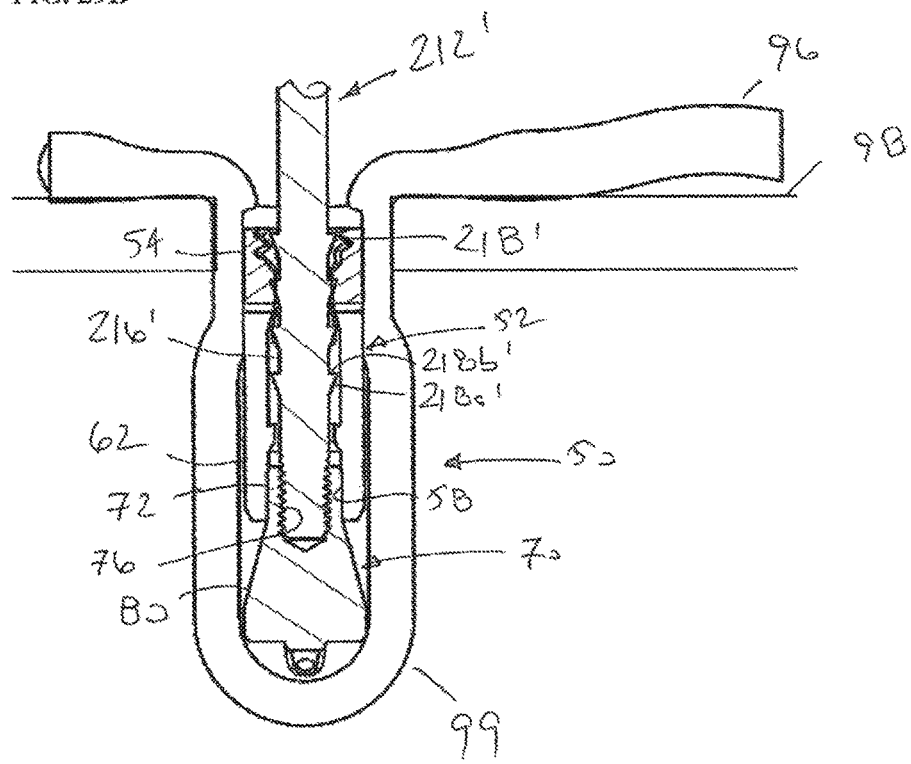
FIG. 30 is a cross-section detail showing an exemplary method for removing a tissue anchor implanted into a bone using a removal tool including the top of FIG. 29B.

Optionally, as shown in FIG. 29A, the distal end 216' of the removal tool may include one or more barbs 218' proximal to the threads 217.' For example, as shown, a plurality of barbs 218' may be spaced apart axially along the shaft 212' for engaging the outer shell 50. For example, as shown in FIG. 30, as the inner shaft 212' is threaded into the expander 70 and then advanced to push the expander 70 out of the outer shell, the barbs 218' may enter the passage 58, e.g., facilitated by tapered distal surfaces 218a' on the barbs 218.' Once the expander 70 is advanced sufficiently, the shaft 212' may be retracted, with blunt proximal surfaces 218b' of the barbs 218' pulling the outer shell 52 simultaneously with the expander 70, thereby preventing the expander from being pulled back into the outer shell 52.

In another option, if the expander 70 includes barbs, detents, or other locking features that engage the proximal end 54 of the outer shell 52, the removal tool 210 (which may any of the embodiments herein) may include one or more features for disengaging the locking feature(s) to allow the expander 70 to be directed distally relative to the outer shell 52. For example, an annular sleeve (not shown) may be provided around the threads 217 that may engage a ramped proximal surface of the locking feature(s) to direct them inwardly or otherwise out of engagement with the outer shell 52. Optionally, the annular sleeve may include a ramped distal edge configured to interact with the locking feature(s) to facilitate disengagement. Once released, the expander 70 may be directed distally back towards its original, distal position, as described elsewhere herein.

Figure 32B:
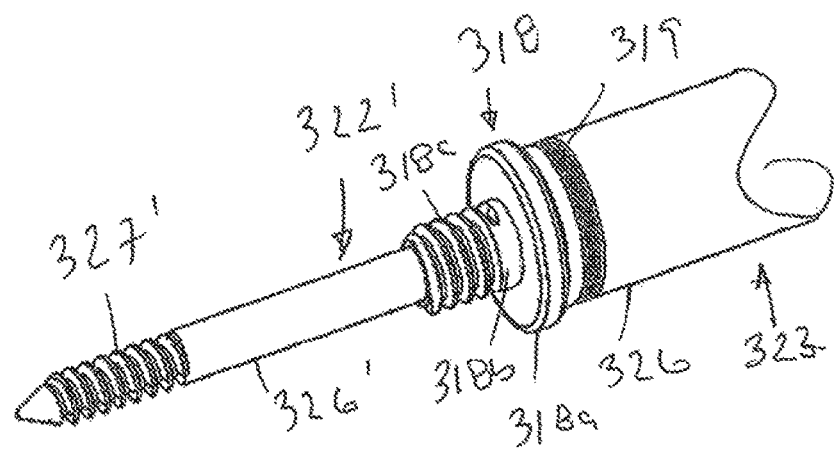

Turning to FIGS. 31A and 31B, yet another example of a removal tool 310 is shown that includes an inner shaft 322 coaxially disposed within an outer shaft 312. The outer shaft 312 includes a proximal end 314 carrying a handle 320 and a distal end 316 carrying an interface or end cap 318 for supporting the outer shell of an anchor (not shown). For example, as shown in FIGS. 32A and 32B, the interface 318 includes a disc 318a and an annular sleeve 318b including one or more threads 318c. In addition or alternatively, the distal end 318 may include a visual marker 319, e.g., spaced a predetermined distance from the interface 318 to facilitate positioning the distal end 318, similar to other embodiments herein.

The inner shaft 322 extends entirely through the outer shaft 312 and handle 320 such that a proximal end 324 thereof is disposed proximal to the handle 320 and a distal end 326 thereof is disposed distal to the outer shaft distal end 316. A secondary handle 330 may be provided on the inner shaft proximal end 322, e.g., such that the handles 320, 322 and shafts 312 322 may be rotated relative to one another. The distal end 326 of the inner shaft 322 includes one or more threads 327 thereon for engaging an expander 70 of an anchor 50, e.g., as shown in FIGS. 33A-33D, similar to the previous embodiments. For example, as shown in FIG. 32A, the threads 327 may be substantially uniform, e.g., having a thread pattern similar to those in the recess 76 of the expander 70. Alternatively, as shown in FIG. 32B, the threads 327' may be self-threading, similar to other embodiments herein.

Figure 33A:
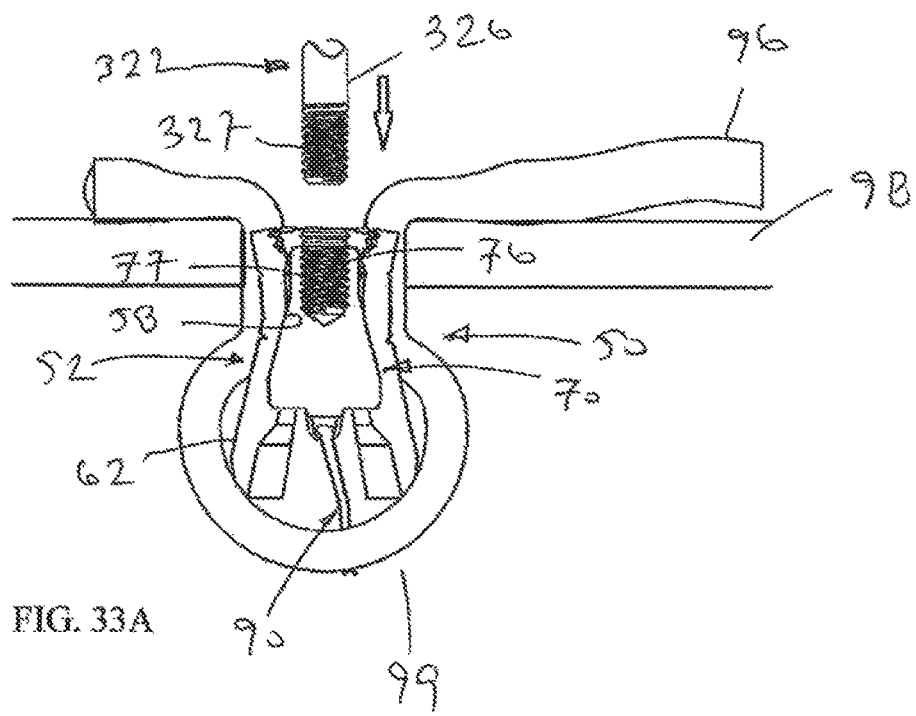
FIGS. 33A-33D show an exemplary method for removing a tissue anchor implanted into a bone using the removal tool of FIGS. 31A and 31B.
Figure 33B:
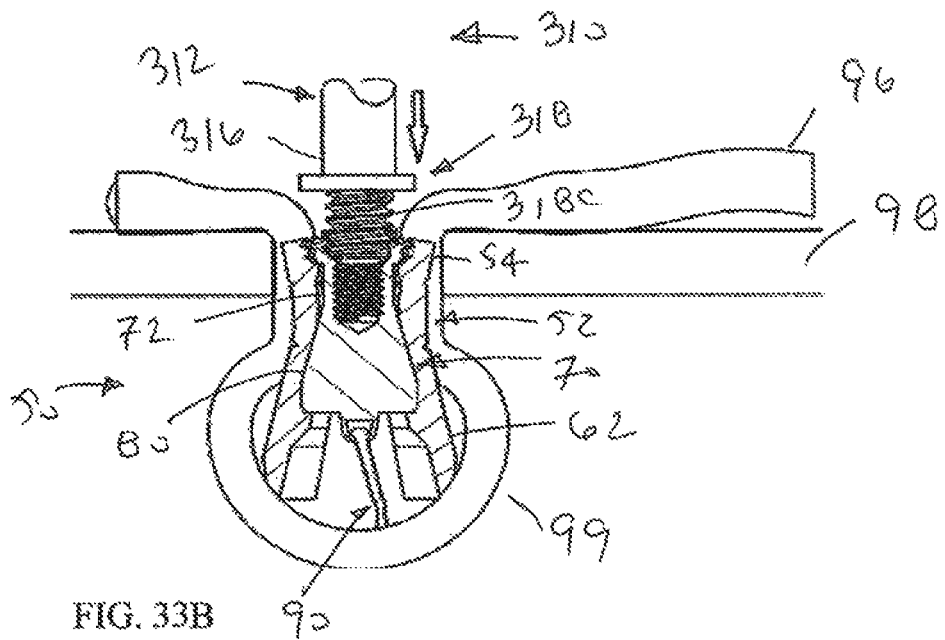

Turning to FIGS. 33A-33D, during use, the removal tool 310 may be used to remove a tissue anchor 50 (which may be any of the embodiments herein) previously implanted into a bone 98. Initially, as shown in FIG. 33A, the distal end 326 of the inner shaft 322 may be inserted into the passage 58 through the outer shell 50 and rotated to thread the threads 327 into the recess 76, i.e., engaging the threads 77 of the expander 70. As shown in FIG. 33B, the outer shaft 312 may then be advanced to insert the threads 318c of the interface 318 into the proximal end 54 of the outer shell 52. For example, the passage 58 may include corresponding threads adjacent the proximal end 54 and the threads 318c may slidably engage such that the sleeve 318b may be inserted into the proximal end 54. Alternatively, the threads 318c may be self-tapping and the sleeve 318b may be threaded into an unthreaded proximal end 54 of the outer shell 52.

Figure 33C:
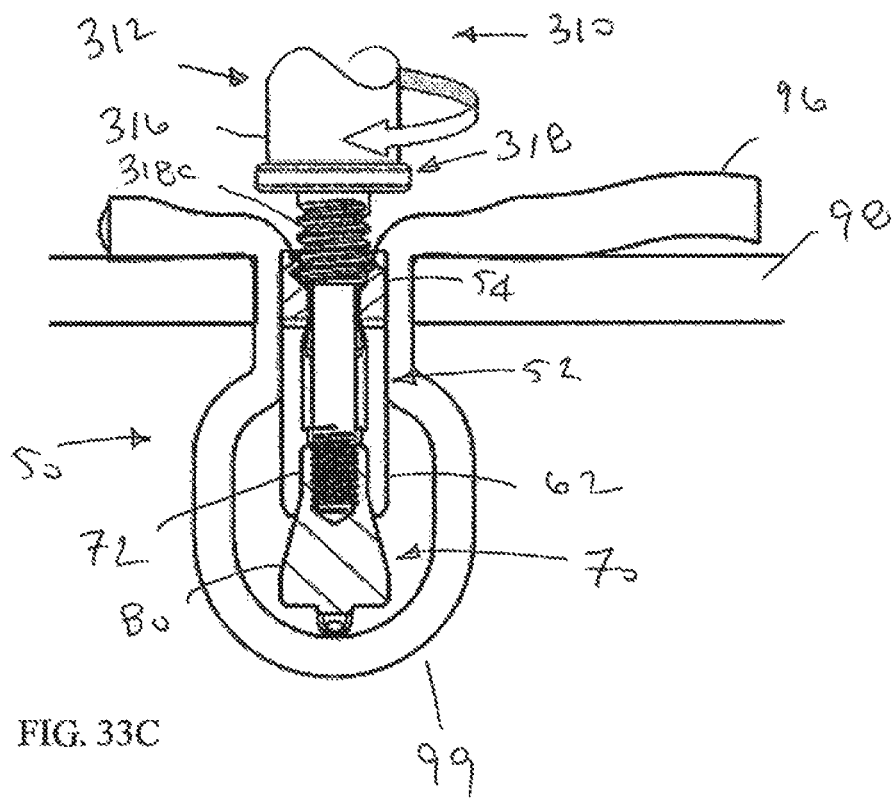
Figure 33D:
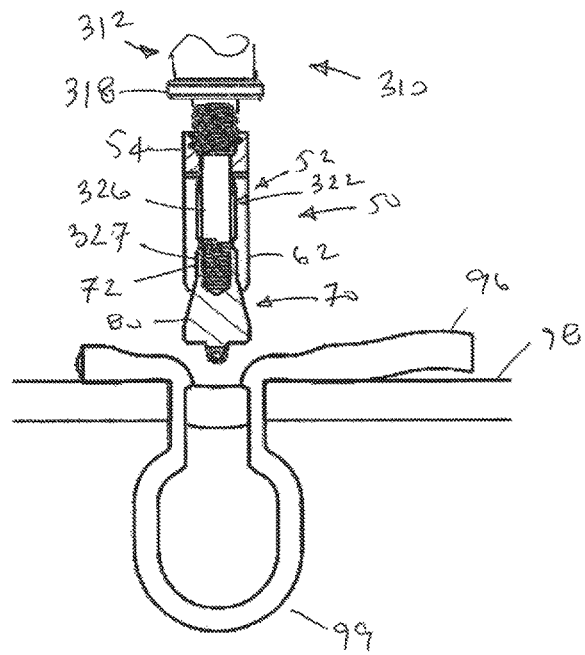

Once both sets of threads 327, 318c are engaged with the expander 70 and outer shell 52, the inner shaft 322 may be advanced without rotation to direct the expander 70 distally to release the arms 62 of the outer shell 52, as shown in FIG. 33C. The entire tool 210 may then be pulled proximally, thereby pulling the anchor 50 out of the bore 99. As with other embodiments, the arms 62 may resiliently retract at least partially or the arms 62 may fold inwardly as the outer shell 52 is pulled from the bore 99, as shown in FIG. 33D.

Figure 34A:
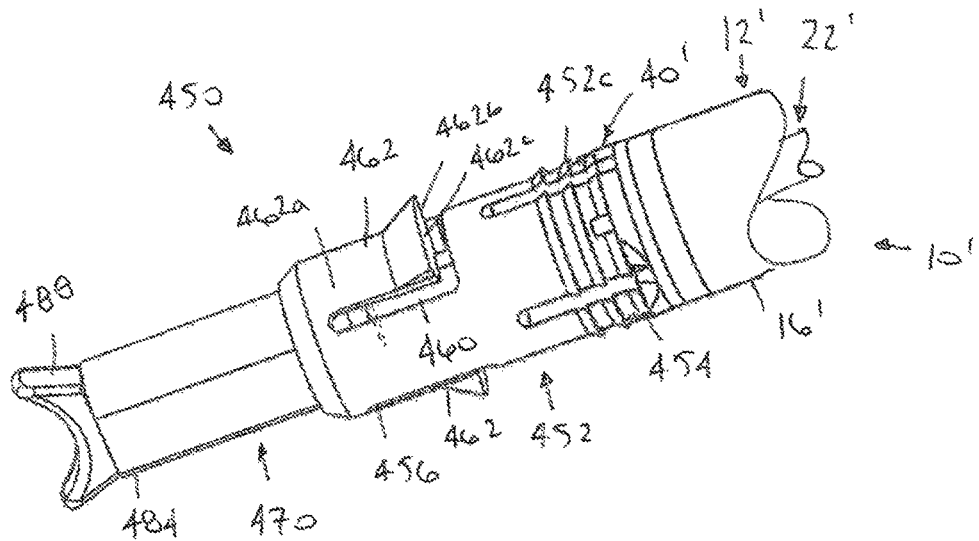
FIGS. 34A and 34B are perspective and exploded views, respectively, of yet another embodiment of a tissue anchor.
Figure 34B:
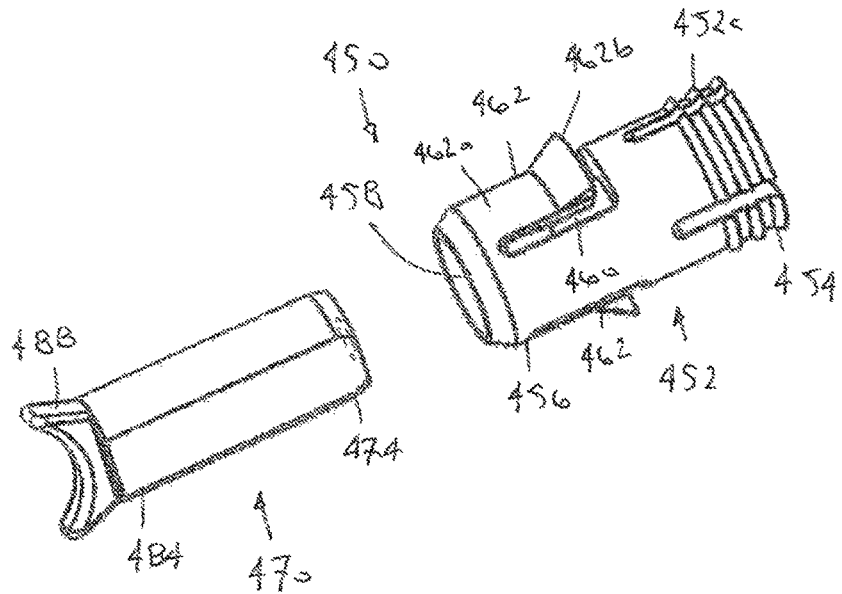

Turning to FIG. 34, another embodiment of an expandable tissue anchor 450 is shown that generally includes an outer shell 452 and an expander 470, generally constructed similar to other embodiments herein. The outer shell 452 is a tubular body including a proximal end 454, a distal end 456, and a passage 458 extending between the proximal and distal ends 454, 456. In the embodiment shown, the outer shell 452 includes a cylindrical outer surface, e.g., defining an outer diameter extending at least partially between the proximal and distal ends 454, 456. Alternatively, the outer shell 452 may have an asymmetrical outer shape, e.g., rectangular, square, or partially cylindrical (not shown), e.g., including opposing planar side surfaces, similar to other embodiments herein.

The passage 458 has an asymmetrical shape, e.g., defining a partially cylindrical, rectangular, or other cross-section, that allows the expander 470 to move axially, e.g., proximally within the passage 458, while preventing rotation, as described further below. Optionally, the outer shell 452 may include one or more ribs or barbs extending outwardly to engage bone, e.g., a plurality of annular ribs 452c adjacent the proximal end 454.

A pair of expandable arms 462 may be provided on opposite sides of the outer shell 452, e.g., defined by one or more slots 460 through the wall of the outer shell 452. For example, the arms 462 may include a first end 462a coupled to the outer shell wall and a second free end 462b proximal to the first end 462a such that the arms 462 are oriented axially. Thus, the arms 462 may act as hinges that may expand outwardly from their original or collapsed configuration to a deployed or expanded configuration. The free end 462b may have a thickness greater than the first end 462a, e.g., defining a blunt proximal end 462c.

In the collapsed configuration, the free ends 462b may extend partially into the passage 458, e.g., to define a reduced cross-section region within the passage 458. Optionally, as best seen in FIG. 35, the passage 458 may include a tapered and/or reduced cross-section proximal region 458a adjacent the proximal end 554, e.g., to limit movement of the expander 470 within the passage 458, as described further below.

The expander 470 is an elongate member including a proximal end 474 and a distal end 484 and defining a substantially uniform width or other cross-section between the proximal and distal ends 474, 484, e.g., similar to the distal portion 458b of the passage 458. In addition, the proximal end 474 includes a recess 476 including one or more threads 477 for coupling to an inner shaft 22' of a delivery tool 10,' and the distal end 484 may include a fork 488 and passages (not shown) for receiving a suture (also not shown), similar to other embodiments herein.

Figure 35:
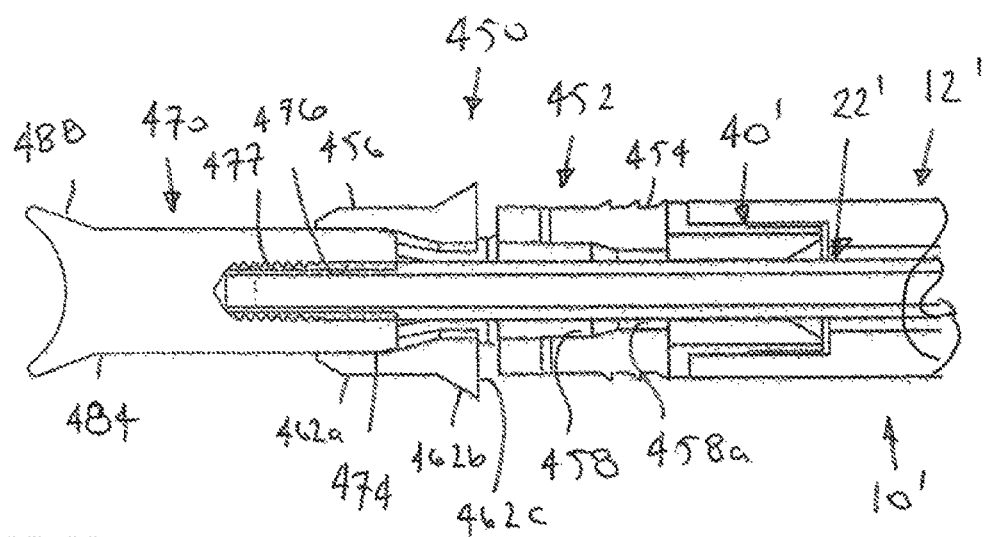
FIG. 35 is a cross-sectional view of the tissue anchor of FIGS. 34A and 34B.
Figure 37:
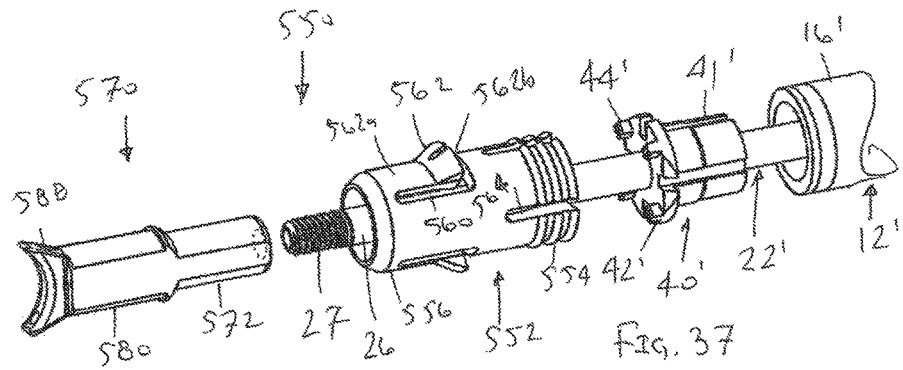
FIG. 37 is a partial exploded view of the tissue anchor of FIG. 36.

In an initial, delivery position, the proximal end 474 of the expander 470 may be disposed within the passage 458 distal to the free ends 462b of the arms 462, e.g., as best seen in FIG. 35, and the distal end 484 and fork 488 may be disposed distally beyond the distal end 456 of the outer shell 452. The anchor 450 may be delivered and deployed similar to other embodiments, e.g., using a tool 10' (which may be any of the embodiments herein) including an outer shaft 12,' inner shaft 22,' and an interface or end cap 40' coupled to the proximal end 454 of the outer shell 452.

Thus, once the anchor 450 is introduced into a bore in bone, e.g., after capturing a tendon in a loop of suture extending from the fork 488 (not shown), the tool 10' may be actuated to direct the inner shaft 22' proximally, thereby directing the expander 470 proximally within the passage 458. As a result of this action, the proximal end 474 of the expander 470 may slidably engage the free ends 462b of the arms 462, thereby causing the arms 462 to hinge or otherwise expand outwardly to the deployed configuration, e.g., to engage adjacent bone (not shown) and secure the anchor 450 within the bore. The expander 470 may continue to move proximally until the proximal end 474 abuts the reduced proximal region 458a of the passage 458, thereby preventing further retraction of the expander 470. The tool 10' may then be disengaged from the anchor 450 and removed, similar to other embodiments herein.

Turning to FIGS. 36-38B, another embodiment of a tissue anchor 550 is shown that includes an outer shell 552, an expander 570, and a suture 90, generally constructed similar to other embodiments herein. The outer shell 552 is a tubular body including a proximal end 554, a distal end 556, and a passage 558 extending between the proximal and distal ends 554, 556. In the embodiment shown, the outer shell 552 includes a cylindrical outer surface, e.g., defining an outer diameter extending at least partially between the proximal and distal ends 554, 556, although, alternatively, the outer shell 552 may have an asymmetrical outer shape, as desired.

Figure 38A:
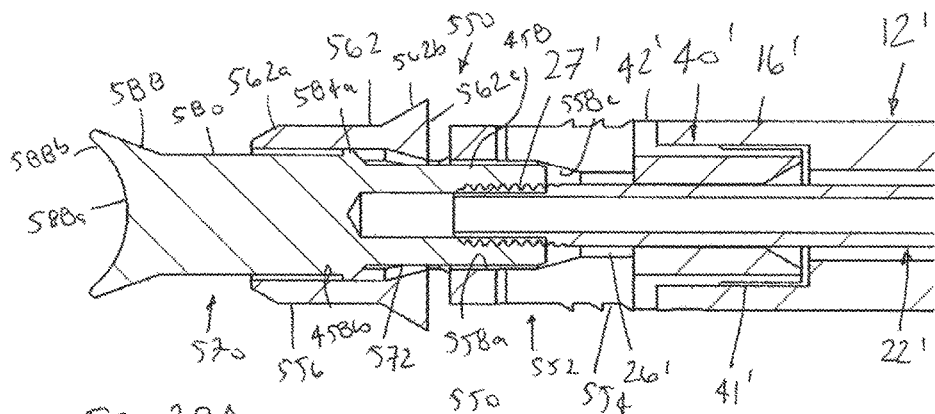
FIGS. 38A and 38B are cross-sectional views of the tissue anchor of FIG. 36 in an original, delivery configuration, and a deployed, expanded configuration, respectively.
Figure 38B:
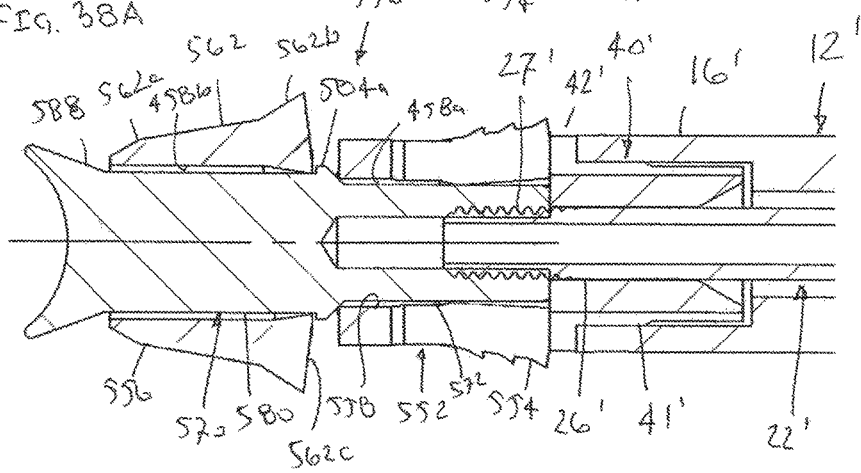

The passage 558 may have an asymmetrical shape, e.g., defining a partially cylindrical, rectangular, or other cross-section, that allows the expander 570 to move axially, e.g., proximally within the passage 558, while preventing rotation, as described further below. As best seen in FIGS. 38A and 38B, the passage 558 may include a proximal region 458a proximal to expandable arms 562 and a distal region 458b between free ends 562b of the arms 562 and the distal end 564.

Similar to the previous embodiment, the outer shell 552 may include a pair of proximally-oriented expandable arms 462, e.g., provided on opposite sides of the outer shell 552, e.g., defined by one or more slots 460 through the wall of the outer shell 452. For example, the arms 562 may include a first end 562a coupled to the outer shell wall and a second free end 562b proximal to the first end 562a such that the arms 562 are oriented axially, with the first end 562a acting as a hinge that may expand outwardly from their original or collapsed configuration to a deployed or expanded configuration. The free end 562b may have a thickness greater than the first end 562a, e.g., defining a blunt proximal end 562c.

The expander 570 is an elongate member including a proximal portion 574, e.g., including a recess 576 with one or more threads 477 for coupling to an inner shaft 22' of a delivery tool 10,' and a distal portion 584 including a fork 588 and passages (not shown) for receiving the suture 90, similar to other embodiments herein. Unlike the previous embodiment, the distal portion 584 may have a larger profile, e.g., width, than the proximal portion 574, and one or more locking features 584a may be provided, e.g., at the transition between the proximal and distal regions 574, 584.

Figure 36:
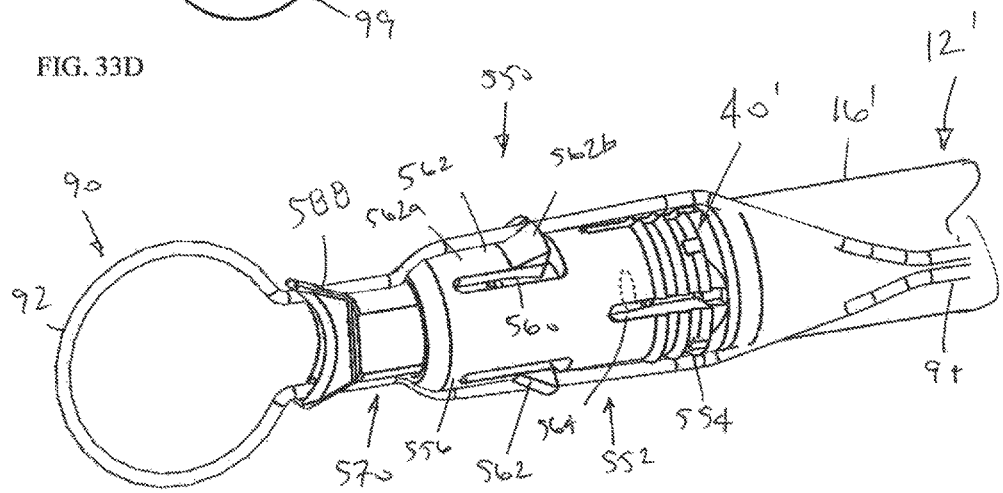
FIG. 36 is a perspective view of another embodiment of a tissue anchor carried on a distal end of a delivery tool.

Initially, the proximal portion 574 of the expander 570 may be disposed within the passage 458, e.g., partially within the proximal and distal regions 558a, 558b, and the distal portion 584 may be disposed partially within the distal region 558b and extending from the distal end 556 of the outer shell 552, as shown in FIGS. 36 and 38A. Thus, in this initial, delivery position, the arms 562 may be disposed inwardly in their original, collapsed configuration. A tool 10' including outer and inner shafts 12', 22' (similar to any of the embodiments herein) may be coupled to the anchor 550 for delivery.

After the anchor 550 is introduced into a bore in a bone, e.g., after capturing a tendon within the suture loop 92 (not shown), the expander 570 may be retracted proximally, e.g., by partially withdrawing inner shaft 22,' to direct the larger distal portion 584 proximally under the free ends 562b of the arms 562, thereby directing the arms 562 outwardly to their expanded configuration, as shown in FIG. 38B. The locking detents 584a may pass proximally beyond the blunt edges 562c of the arms 562 (e.g., into a region of the slots 560), thereby preventing the expander 570 from subsequently returning distally, thereby locking the arms 562 in the expanded configuration to engage adjacent bone and/or otherwise secure the anchor 550 within the bore.

Optionally, as best seen in FIGS. 38A and 38B, the passage 558 may include a narrower region 558a adjacent the proximal end 554 of the outer shell 552 into which the proximal portion 574 of the expander 570 is directed during retraction. If the outer shell includes proximal slots 564, the slots 564 allow the proximal end 554 of the outer shell 562 to expand outwardly, as shown in FIG. 38B, during retraction of the expander 570, thereby further engaging adjacent bone and securing the anchor 550. The tool 10' may then be disengaged and removed, similar to other embodiments herein.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the devices described herein may be combined with any of the delivery systems and methods also described herein.

While embodiments of the present invention have been shown and described, various modifications may be made without departing from the scope of the present invention. The invention, therefore, should not be limited, except to the following claims, and their equivalents.

I claim:

1. A tissue anchor for securing a tissue structure to bone, comprising:
    an outer shell including a proximal end, a distal end sized for introduction into a bore in bone, a passage extending between the proximal and distal ends defining a longitudinal axis therebetween, a pair of opposing planar outer surfaces extending axially at least partially between the proximal and distal ends of the outer shell, the planar surfaces oriented parallel to a plane, and a plurality of distal slots extending proximally from the distal end to define a plurality of expandable arms;
    an expander including a uniform cross-section proximal portion and a ramped distal portion, the proximal portion disposed within the passage such that the distal portion extends distally from the outer shell distal end in a delivery position, the expander movable proximally relative to the outer shell to a deployed position wherein the distal portion enters the passage, thereby directing the plurality of arms outwardly to engage bone adjacent the bore; and
    a loop extending from the distal portion of the expander for capturing a tissue structure,
    wherein the distal portion of the expander has an oval cross-section defining a major axis and a minor axis, the major axis oriented parallel to the plane, and
    wherein the expander and the outer shell include cooperating alignment features that allow axial movement while preventing rotation relative to one another.

2. The tissue anchor of claim 1, further comprising a fork extending distally from the distal portion of the expander, the fork including a pair of tines spaced apart from one another and a concave distal surface extending between the tines.

3. The tissue anchor of claim 2, wherein the fork includes a distal opening adjacent each tine and the expander includes side openings on opposite sides of the distal portion, and wherein the loop includes loop ends extending from the loop into the distal openings and out the side openings into the outer shell, the loop ends slidable within the openings to adjust a size of the loop.

4. The tissue anchor of claim 3, wherein the distal slots in the outer shell comprise axial passages slidably receiving the loop ends to limit rotation of the expander relative to the outer shell.

5. The tissue anchor of claim 3, wherein the distal slots in the outer shell comprise axial passages slidably receiving the loop ends to allow the loop ends to slide axially along the outer shell.

6. The tissue anchor of claim 2, wherein the tines of the fork are spaced apart by a distance smaller than the major axis distance.

7. The tissue anchor of claim 2, wherein the tines of the fork are spaced apart by a distance larger than the major axis distance.

8. The tissue anchor of claim 1, wherein the outer shell includes one or more outwardly oriented barbs or ribs to engage adjacent tissue.

9. The tissue anchor of claim 1, wherein the outer shell includes a plurality of proximal slots extending distally from the proximal end such that the outer shell proximal end expands outwardly as the expander is directed from the delivery position to the deployed position.

10. The tissue anchor of claim 1, wherein each of the arms include one or more hinges to accommodate outward expansion of the arms.

11. The tissue anchor of claim 1, wherein the outer shell and expander include one or more locking elements that prevent the expander from moving from the deployed position back towards the delivery position.

12. A tissue anchor for securing a tissue structure to bone, comprising:
    an outer shell including a proximal end, a distal end sized for introduction into a bore in bone, a passage extending between the proximal and distal ends defining a longitudinal axis therebetween, a pair of planar outer surfaces on opposite sides of the outer shell and extending axially at least partially between the proximal and distal ends of the outer shell, the planar surfaces oriented parallel to a plane, the outer shell further comprising a plurality of distal slots extending proximally from the distal end to define a plurality of expandable arms;

an expander including a uniform cross-section proximal portion and a ramped distal portion, the proximal portion disposed within the passage such that the distal portion extends distally from the outer shell distal end in a delivery position, the expander movable proximally relative to the outer shell to a deployed position wherein the distal portion at least partially enters the passage, thereby directing the plurality of arms outwardly to engage bone adjacent the bore; and a loop extending from the distal portion of the expander for capturing a tissue structure, wherein the distal portion of the expander has an oval cross-section defining a major axis and a minor axis, the major axis oriented parallel to the plane.

* * * * *